United States Patent
Angibaud et al.

(10) Patent No.: US 7,196,094 B2
(45) Date of Patent: *Mar. 27, 2007

(54) FARNESYL TRANSFERASE INHIBITING 6-HETEROCYCLYLMETHYL QUINOLINE AND QUINAZOLINE DERIVATIVES

(75) Inventors: Patrick René Angibaud, Fontaine-Bellenger (FR); Marc Gaston Venet, Le Mesnil-Esnard (FR); Laurence Anne Mevellec, Louviers (FR)

(73) Assignee: Janssen Pharmaceutica, N.V. (BE)

( * ) Notice: Subject to any disclaimer, the term of this patent is extended or adjusted under 35 U.S.C. 154(b) by 335 days.

This patent is subject to a terminal disclaimer.

(21) Appl. No.: 10/381,361

(22) PCT Filed: Sep. 18, 2001

(86) PCT No.: PCT/EP01/10894

§ 371 (c)(1), (2), (4) Date: Mar. 24, 2003

(87) PCT Pub. No.: WO02/24686

PCT Pub. Date: Mar. 28, 2002

(65) Prior Publication Data

US 2003/0207887 A1    Nov. 6, 2003

(30) Foreign Application Priority Data

Sep. 25, 2000 (EP) .................................. 00203368
Jun. 7, 2001 (EP) .................................. 01202190

(51) Int. Cl.
C07D 487/04 (2006.01)
C07D 471/04 (2006.01)
A61K 31/395 (2006.01)

(52) U.S. Cl. ........................... 514/266.21; 514/266.23; 514/267; 544/252; 544/284

(58) Field of Classification Search ................ 544/252, 544/284; 514/266.21, 266.23, 267
See application file for complete search history.

(56) References Cited

U.S. PATENT DOCUMENTS 6,458,800 B1 * 10/2002 Angibaud et al. .......... 514/267
6,914,066 B2 * 7/2005 Angibaud et al. .......... 514/267

FOREIGN PATENT DOCUMENTS

EP    0371564 B1    6/1990
WO    WO 97/16443 A2    5/1997
WO    WO 97/21701 A1    6/1997
WO    WO 98/40383 A1    9/1998
WO    WO 98/49157 A1    11/1998
WO    WO 98/55124 A1    12/1998
WO    WO 00/01386 A1    1/2000
WO    WO 00/01411 A1    1/2000
WO    WO 00/12498 A1    3/2000
WO    WO 00/12499 A1    3/2000
WO    WO 00/39082 A2    7/2000
WO    WO 00/47574 A1    8/2000

OTHER PUBLICATIONS

Simone, Oncology: Introduction, Cecil Textbook of Medicine, 20th Edition, vol. 1, pp. 1004-1010, 1996.*
Nielsen et al., Combination Therapy with the Farnesyl Protein Transferase Inhibitor SCH66336 and SCH58500 (p53 Adenovirus) in Preclinical Cancer Models, Cancer Research, 59, pp. 5896-5901, Dec. 1999.*
Tagawa, PubMed Abstract (Curr Pharm Des. 6(6):681-99) Apr. 2000.*
Kohl et al., "Selective Inhibition of ras-Dependent Transformation by a Farnesyltransferase Inhibitor," *Science*, 1993, pp. 1934-1937, vol. 260, No. 5116.
Rak et al., "Mutant ras Oncogenes Upregulate VEGF/VPF Expression: Implications for Induction and Inhibition of Tumor Angiogenesis." *Cancer Research*, 1995, pp. 4575-4580, vol. 55, No. 20.

* cited by examiner

*Primary Examiner*—Deepak Rao

(57) ABSTRACT

This invention comprises the novel compounds of formula (I)

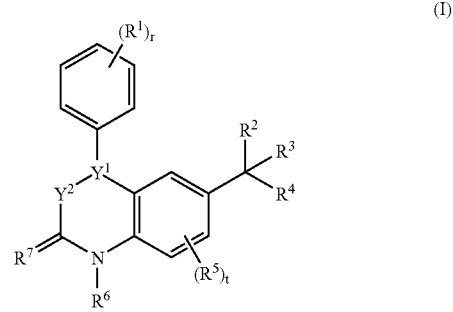

wherein r, t, $Y^1$—$Y^2$, $R^1$, $R^2$, $R^3$, $R^4$, $R^5$, $R^6$ and $R^7$ have defined meanings, having farnesyl transferase inhibiting activity; their preparation, compositions containing them and their use as a medicine.

9 Claims, No Drawings

FARNESYL TRANSFERASE INHIBITING 6-HETEROCYCLYLMETHYL QUINOLINE AND QUINAZOLINE DERIVATIVES

CROSS REFERENCE TO RELATED APPLICATIONS

This application is the national stage of Application No. PCT/EP018945, filed Sep. 18, 2001 which application claims priority from EP 00203368.6 filed Sep. 25, 2000, and EP 01202190.3 filed Jun. 7, 2001.

The present invention is concerned with novel 6-heterocyclylmethyl quinoline and quinazoline derivatives, the preparation thereof, pharmaceutical compositions comprising said novel compounds and the use of these compounds as a medicine as well as methods of treatment by administering said compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzymes that catalyzes this modification, i.e. farnesyl transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to transformation.

Since mutated oncogenic forms of ras are frequently found in many human cancers, most notably in more than 50% of colon and pancreatic carcinomas (Kohl et al., Science, vol 260, 1834–1837, 1993), it has been suggested that farnesyl tranferase inhibitors can be very useful against these types of cancer.

In EP-0,371,564 there are described (1H-azol-1-ylmethyl) substituted quinoline and quinolinone derivatives which suppress the plasma elimination of retinoic acids. Some of these compounds also have the ability to inhibit the formation of androgens from progestines and/or inhibit the action of the aromatase enzyme complex.

In WO 97/16443, WO 97/21701, WO 98/40383 and WO 98/49157, there are described 2-quinolinones and 2-quinazolinones derivatives which exhibit farnesyl transferase inhibiting activity. WO 00/39082 describes a class of novel 1,2-annelated quinoline compounds, bearing a nitrogen- or carbon-linked imidazole, which show farnesyl protein transferase and geranylgeranyl transferase inhibiting activity. Other quinolone compounds having farnesyl transferase inhibiting activity are described in WO 00/12498, 00/12499 and 00/47574.

Unexpectedly, it has been found that the present novel 6-heterocyclylmethyl quinoline and quinazoline compounds show farnesyl protein transferase inhibiting activity.

The present invention concerns compounds of formula (I):

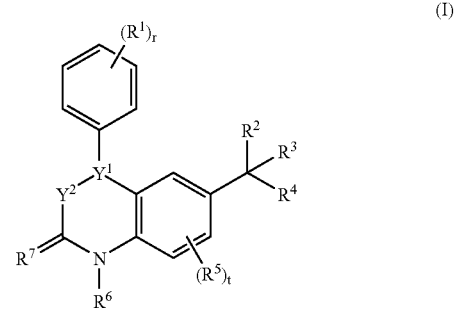

or a pharmaceutically acceptable salt or N-oxide or stereochemically isomeric form thereof, wherein r is 0, 1, 2, 3, 4 or 5;

t is 0, 1, 2 or 3;

$>Y^1-Y^2-$ is a trivalent radical of formula

| | |
|---|---|
| $>C=N-$ | (y-1) |
| $>C=CR^9-$ | (y-2) |
| $>CH-NR^9-$ | (y-3) |
| $>CH-CHR^9-$ | (y-4) | wherein $R^9$ is hydrogen, halo, cyano, $C_{1-6}$alkyl, hydroxy$C_{1-6}$alkyl, $C_{1-6}$alkyloxy$C_{1-6}$alkyl, $-(CR^{20}R^{21})_p-C_{3-10}$cycloalkyl, $C_{2-6}$alkenyl, $C_{2-6}$alkynyl, $C_{1-6}$alkyloxy, halocarbonyl, hydroxycarbonyl, $C_{1-6}$alkyloxycarbonyl, aryl or a group of formula $-NR^{22}R^{23}$, $-C_{1-6}$alkyl-$NR^{22}R^{23}$, $-C_{2-6}$alkenyl-$NR^{22}R^{23}$, $-CONR^{22}R^{23}$ or $-NR^{22}-C_{1-6}$alkyl-$NR^{22}R^{23}$;

p is 0 to 5;

$R^{20}$ and $R^{21}$ are independently hydrogen or $C_{1-6}$ alkyl and are independently defined for each iteration of p in excess of 1;

$R^{22}$ and $R^{23}$ are independently hydrogen, $C_{1-6}$ alkyl or $-(CR^{20}R^{21})_p-C_{3-10}$cycloalkyl, or together with the adjacent nitrogen atom form a 5- or 6-membered heterocyclic ring optionally containing one, two or three further heteroatoms selected from oxygen, nitrogen or sulphur and optionally substituted by one or two substituents each independently selected from halo, hydroxy, cyano, nitro, $C_{1-6}$alkyl, halo$C_{1-6}$alkyl, $C_{1-6}$alkyloxy, $OCF_3$, hydroxycarbonyl, $C_{1-6}$alkyloxycarbonyl, aminocarbonyl, mono- or di-($C_{1-6}$alkyl)aminocarbonyl, amino, mono- or di($C_{1-6}$alkyl)amino, $C_{1-6}$alkylsulfonylamino, oxime, or phenyl;

$R^1$ is azido, hydroxy, halo, cyano, nitro, $C_{1-6}$alkyl, $-(CR^{20}R^{21})_p-C_{3-10}$cycloalkyl, cyano$C_{1-6}$alkyl, hydroxy$C_{1-6}$alkyl, $C_{1-6}$alkyloxy$C_{1-6}$alkyl, hydroxycarbonyl$C_{1-6}$alkyloxy$C_{1-6}$alkyl, $R^{24}S$ $C_{1-6}$alkyl, trihalomethyl, aryl$C_{1-6}$alkyl, $Het^2C_{1-6}$alkyl, $-C_{1-6}$alkyl-$NR^{22}R^{23}$, $-C_{1-6}$alkylNR$^{22}C_{1-6}$alkyl-$NR^{22}R^{23}$, $-C_{1-6}$alkylNR$^{22}$COC$_{1-6}$alkyl, $-C_{1-6}$alkylNR$^{22}$COAlkAr$^2$, $-C_{1-6}$alkylNR$^{22}$COAr$^2$, $C_{1-6}$alkylsulphonylamino$C_{1-6}$alkyl, $C_{1-6}$alkyloxy, hydroxy$C_{1-6}$alkyloxy, $C_{1-6}$alkyloxy$C_{1-6}$alkyloxy, $-OC_{1-6}$alkyl-$NR^{22}R^{23}$, trihalomethoxy, arylC$_{1-6}$alkyloxy, Het$^2$C$_{1-6}$alkyloxy, C$_{1-6}$alkylthio, C$_{2-6}$alkenyl, cyanoC$_{2-6}$alkenyl, —C$_{2-6}$alkenyl-NR$^{22}$R$^{23}$, hydroxycarbonylC$_{2-6}$alkenyl, C$_{1-6}$alkyloxycarbonylC$_{2-6}$alkenyl, C$_{2-6}$alkynyl, —CHO, C$_{1-6}$alkylcarbonyl, hydroxyC$_{1-6}$alkylcarbonyl, hydroxycarbonyl, C$_{1-6}$alkyloxycarbonyl, —CONR$^{22}$R$^{23}$, —CONR$^{22}$—C$_{1-6}$alkyl-NR$^{22}$R$^{23}$, —CONR$^{22}$—C$_{1-6}$alkyl-Het$^2$, —CONR$^{22}$—C$_{1-6}$alkyl-Ar$^2$, —CONR$^{22}$—O—C$_{1-6}$alkyl, —CONR$^{22}$—C$_{1-6}$alkenyl, —NR$^{22}$R$^{23}$, —OC(O)R$^{24}$, —CR$^{24}$=NR$^{25}$, —CR$^{24}$=N—OR$^{25}$, —NR$^{24}$C(O)NR$^{22}$R$^{23}$, —NR$^{24}$SO$_2$R$^{25}$, —NR$^{24}$C(O)R$^{25}$, —S(O)$_{0-2}$R$^{24}$, —SO$_2$NR$^{24}$R$^{25}$, —C(NR$^{26}$R$^{27}$)=NR$^{28}$; —Sn(R$^{24}$)$_3$, —SiR$^{24}$R$^{24}$R$^{25}$, —B(OR$^{24}$)$_2$, —P(O)OR$^{24}$OR$^{25}$, aryloxy, Het$^2$-oxy, or a group of formula —Z, —CO—Z or —CO—NR$^y$—Z in which R$^y$ is hydrogen or C$_{1-4}$alkyl and Z is phenyl or a 5- or 6-membered heterocyclic ring containing one or more heteroatoms selected from oxygen, sulphur and nitrogen, the phenyl or heterocyclic ring being optionally substituted by one or two substituents each independently selected from halo, cyano, hydroxycarbonyl, aminocarbonyl, C$_{1-6}$alkylthio, hydroxy, —NR$^{22}$R$^{23}$, C$_{1-6}$alkylsulphonylamino, C$_{1-6}$alkyl, haloC$_{1-6}$alkyl, C$_{1-6}$alkyloxy or phenyl; or two R$^1$ substituents adjacent to one another on the phenyl ring may form together a bivalent radical of formula

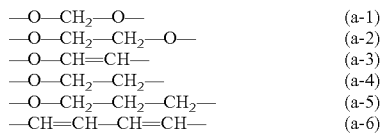

| | |
|---|---|
| —O—CH$_2$—O— | (a-1) |
| —O—CH$_2$—CH$_2$—O— | (a-2) |
| —O—CH=CH— | (a-3) |
| —O—CH$_2$—CH$_2$— | (a-4) |
| —O—CH$_2$—CH$_2$—CH$_2$— | (a-5) |
| —CH=CH—CH=CH— | (a-6) |

R$^{24}$ and R$^{25}$ are independently hydrogen, C$_{1-6}$ alkyl, —(CR$_{20}$R$_{21}$)p-C$_{3-10}$cycloalkyl or arylC$_{1-6}$alkyl;

R$^{26}$, R$^{27}$ and R$^{28}$ are independently hydrogen and C$_{1-6}$alkyl or C(O) C$_{1-6}$alkyl;

R$^2$ is a mono- or bi-cyclic heterocyclic ring containing one or more heteroatoms selected from oxygen, sulphur and nitrogen and optionally substituted by one or two substituents each independently selected from halo, cyano, hydroxy, nitro, C$_{1-6}$alkyl, haloC$_{1-6}$alkyl, -alkylNR$^{22}$R$^{23}$, C$_{1-6}$alkyloxy, OCF$_3$, hydroxycarbonyl, C$_{1-6}$alkyloxycarbonyl, —CONR$^{22}$R$^{23}$, —NR$^{22}$R$^{23}$, C$_{1-6}$alkylsulfonylamino, oxime, phenyl or benzyl;

R$^3$ is hydrogen, halo, cyano, C$_{1-6}$alkyl, —(CR$^{20}$R$^{21}$)$_p$— C$_{3-10}$cycloalkyl, haloC$_{1-6}$alkyl, cyanoC$_{1-6}$alkyl, hydroxyC$_{1-6}$alkyl, C$_{1-6}$alkyloxyC$_{1-6}$alkyl, arylC$_{1-6}$alkyloxyC$_{1-6}$alkyl, C$_{1-6}$alkylthioC$_{1-6}$alkyl, hydroxycarbonylC$_{1-6}$alkyl, C$_{1-6}$alkylcarbonylC$_{1-6}$alkyl, C$_{1-6}$alkyloxycarbonylC$_{1-6}$ alkyl, —C$_{1-6}$alkyl-NR$^{22}$R$^{23}$, —C$_{1-6}$alkyl-CONR$^{22}$R$^{23}$, arylC$_{1-6}$alkyl, Het$^2$C$_{1-6}$alkyl, C$_{2-6}$alkenyl, —C$_{2-6}$alkenyl, NR$^{22}$R$^{23}$, C$_{2-6}$alkynyl, hydroxycarbonyl, C$_{1-6}$alkyloxycarbonyl, aryl, or Het$^2$; or a radical of formula

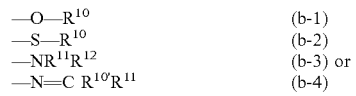

| | |
|---|---|
| —O—R$^{10}$ | (b-1) |
| —S—R$^{10}$ | (b-2) |
| —NR$^{11}$R$^{12}$ | (b-3) or |
| —N=C R$^{10'}$R$^{11}$ | (b-4) | wherein

R$^{10}$ is hydrogen, C$_{1-6}$alkyl, —(CR$^{20}$R$^{21}$)$_p$—C$_{3-10}$cycloalkyl, arylC$_{1-6}$alkyl, C$_{2-6}$alkenyl, C$_{2-6}$alkynyl, C$_{1-6}$alkylcarbonyl, aryl, a group of formula —NR$^{22}$R$^{23}$R or —C$_{1-6}$alkylC(O)OC$_{1-6}$alkyl NR$^{22}$R$^{23}$, or a radical of formula -Alk-OR$^{13}$ or -Alk-NR$^{14}$R$^{15}$;

R$^{10'}$ is hydrogen, C$_{1-6}$alkyl, —(CR$^{20}$R$^{21}$)$_p$—C$_{3-10}$cycloalkyl, arylC$_{1-6}$alkyl, aryl or a group of formula —NR$^{22}$R$^{23}$;

R$^{11}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, aryl or arylC$_{1-6}$alkyl;

R$^{12}$ is hydrogen, hydroxy, C$_{1-6}$alkyl, —(CR$^{20}$R$^{21}$)$_p$—C$_{3-10}$cycloalkyl, C$_{1-6}$alkylcarbonylC$_{1-6}$alkyl, arylC$_{1-6}$alkyl, C$_{2-6}$alkenyl, C$_{2-6}$alkynyl, aryl, C$_{1-6}$alkyloxy, a group of formula —NR$^{22}$R$^{23}$, C$_{1-6}$alkylcarbonylamino, C$_{1-6}$alkylcarbonyl, haloC$_{1-6}$alkylcarbonyl, arylC$_{1-6}$alkylcarbonyl, Het$^2$C$_{1-6}$alkylcarbonyl, arylcarbonyl, C$_{1-6}$alkyloxycarbonyl, trihalo C$_{1-6}$alkyloxycarbonyl, C$_{1-6}$alkyloxyC$_{1-6}$alkylcarbonyl, aminocarbonyl, mono- or di(C$_{1-6}$alkyl)aminocarbonyl wherein the alkyl moiety may optionally be substituted by one or more substituents independently selected from aryl and C$_{1-6}$alkyloxycarbonyl substituents; aminocarbonylcarbonyl, mono- or di(C$_{1-}$di(C$_{1-6}$alkyl) aminoC$_{1-6}$alkylcarbonyl, or a radical of formula -Alk-OR$^{13}$ or Alk-NR$^{14}$R$^{15}$; wherein Alk is C$_{1-6}$alkanediyl;

R$^{13}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, C$_{1-6}$alkylcarbonyl, hydroxyC$_{1-6}$alkyl, aryl or arylC$_{1-6}$alkyl;

R$^{14}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, aryl or arylC$_{1-6}$alkyl;

R$^{15}$ is hydrogen, C$_{1-6}$alkyl, —(CR$^{20}$R$^{21}$)$_p$—C$_{3-10}$cycloalkyl, C$_{2-6}$alkenyl, C$_{2-6}$alkynyl, C$_{1-6}$alkylcarbonyl, aryl or arylC$_{1-6}$alkyl;

R$^4$ is a radical of formula

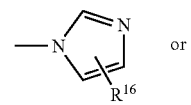

(c-1) or

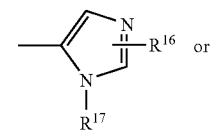

(c-2) or

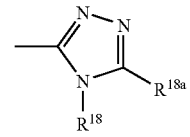

(c-3)

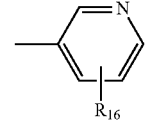

(c-4)

wherein R$^{16}$ is hydrogen, halo, C$_{1-6}$alkyl, —(CR$^{20}$R$^{21}$)$_p$—C$_{3-10}$cycloalkyl, hydroxyC$_{1-6}$alkyl, C$_{1-6}$alkyloxyC$_{1-6}$alkyl, C$_{1-6}$alkylS(O)$_{0-2}$C$_{1-6}$alkyl, C$_{1-6}$alkyloxy, C$_{1-6}$alkylthio, a group of formula —NR$^{22}$R$^{23}$, hydroxycarbonyl, C$_{1-6}$alkyloxycarbonyl or aryl, R$^{17}$ is hydrogen, C$_{1-6}$alkyl, —(CR$^{20}$R$^{21}$)$_p$—C$_{3-10}$cycloalkyl, hydroxyC$_{1-6}$alkyl, C$_{1-6}$alkyloxyC$_{1-6}$alkyl, aryl C$_{1-6}$alkyl, trifluoromethyl, trifluoromethylC$_{1-6}$alkyl, hydroxycarbonylC$_{1-6}$alkyl, C$_{1-6}$alkyloxycarbonylC$_{1-6}$alkyl, mono- or di(C$_{1-6}$alkyl)aminosulphonyl or —C$_{1-6}$alkylP(O)OR$^{24}$OR$^{25}$;

R$^{18}$ is hydrogen, C$_{1-6}$alkyl, —(CR$^{20}$R$^{21}$)$_p$—C$_{3-10}$cycloalkyl, arylC$_{1-6}$alkyl or C$_{1-6}$alkyloxyC$_{1-6}$alkyl;

R$^{18a}$ is hydrogen, —SH or —SC$_{1-4}$alkyl;

R$^5$ is cyano, hydroxy, halo, C$_{1-6}$alkyl, —(CR$^{20}$R$^{21}$)$_p$—C$_{3-10}$cycloalkyl, C$_{2-6}$alkenyl, C$_{2-6}$alkynyl, C$_{1-6}$alkyloxy, arylC$_{1-6}$alkyloxy, Het$^2$C$_{1-6}$alkyloxy, hydroxycarbonyl, C$_{1-6}$alkyloxycarbonyl, or a group of formula —NR$^{22}$R$^{23}$ or —CONR$^{22}$R$^{23}$;

R$^6$ is hydrogen, C$_{1-6}$alkyl, —(CR$^{20}$R$^{21}$)$_p$—C$_{3-10}$cycloalkyl, cyanoC$_{1-6}$alkyl, —C$_{1-6}$alkylCO$_2$R$^{24}$, aminocarbonylC$_{1-6}$alkyl or —C$_{1-6}$alkyl-NR$^{22}$R$^{23}$, R$^{24}$SO$_2$, R$^{24}$SO$_2$C$_{1-6}$alkyl, —C$_{1-6}$alkyl-OR$^{24}$, —C$_{1-6}$alkyl-SR$^{24}$, —C$_{1-6}$alkyl-CONR$^{22}$—C$_{1-6}$alkyl-NR$^{22}$R$^{23}$, —C$_{1-6}$alkylCONR$^{22}$—C$_{1-6}$alkyl-Het$^2$, —C$_{1-6}$alkylCONR$^{22}$—C$_{1-6}$alkyl-Ar$^2$, —C$_{1-6}$alkyl CONR$^{22}$-Het$^2$, —C$_{1-6}$alkylCONR$^{22}$Ar$^2$, —C$_{1-6}$alkylCONR$^{22}$—O—C$_{1-6}$alkyl, —C$_{1-6}$alkyl-CONR$^{22}$—C$_{1-6}$alkenyl, -Alk-Ar$^2$ or -AlkHet$^2$;

R$^7$ is oxygen or sulphur; or R$^6$ and R$^7$ together form a trivalent radical of formula:

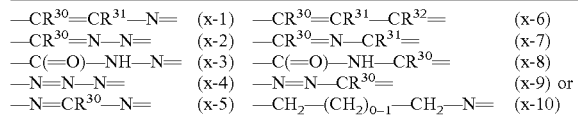

| | | | |
|---|---|---|---|
| —CR$^{30}$=CR$^{31}$—N= | (x-1) | —CR$^{30}$=CR$^{31}$—CR$^{32}$= | (x-6) |
| —CR$^{30}$=N—N= | (x-2) | —CR$^{30}$=N—CR$^{31}$= | (x-7) |
| —C(=O)—NH—N= | (x-3) | —C(=O)—NH—CR$^{30}$= | (x-8) |
| —N=N—N= | (x-4) | —N=N—CR$^{30}$= | (x-9) or |
| —N=CR$^{30}$—N= | (x-5) | —CH$_2$—(CH$_2$)$_{0-1}$—CH$_2$—N= | (x-10) | wherein each R$^{30}$, R$^{31}$ and R$^{32}$ are independently hydrogen, C$_{1-6}$ alkyl, —OR$^{24}$, —COOR$^{24}$, —NR$^{22}$R$^{23}$, —C$_{1-6}$alkylOR$^{24}$, —C$_{1-6}$ alkylSR$^{24}$, R$^{23}$R$^{22}$NC$_{1-6}$alkyl-, —CONR$^{22}$R$^{23}$, C$_{2-6}$alkenyl, C$_{2-6}$alkenylAr$^2$, C$_{2-6}$alkenylHet$^2$, cyano, amino, thio, C$_{1-6}$ alkylthio, —O—Ar$^2$, —S—Ar$^2$ or Ar$^2$;

Ar$^2$ is phenyl, naphthyl or phenyl or naphthyl substituted by one to five substituents each independently selected from halo, hydroxy, cyano, nitro, C$_{1-6}$alkyl, haloC$_{1-6}$alkyl, -alkylNR$^{22}$R$^{23}$, C$_{1-6}$alkyloxy, OCF$_3$, hydroxycarbonyl, C$_{1-6}$alkyloxycarbonyl, aryloxy, —NR$^{22}$R$^{23}$, C$_{1-6}$alkylsulfonylamino, oxime or phenyl, or a bivalent substituent of formula —O—CH$_2$—O— or —O—CH$_2$—CH$_2$—O—;

Het$^2$ is a mono- or bi-cyclic heterocyclic ring containing one or more heteroatoms selected from oxygen, sulphur and nitrogen and optionally substituted by one or two substituents each independently selected from halo, hydroxy, cyano, nitro, C$_{1-6}$alkyl, haloC$_{1-6}$alkyl, -alkylNR$^{22}$R$^{23}$, C$_{1-6}$alkyloxy, OCF$_3$, hydroxycarbonyl, C$_{1-6}$alkyloxycarbonyl, —CONR$^{22}$R$^{23}$, —NR$^{22}$R$^{23}$, C$_{1-6}$alkylsulfonylamino, oxime or phenyl;

provided that when >Y$^1$—Y$^2$ is a radical of formula (y-2) or (y-4) and (a) R$^4$ is a radical of formula (c-1), (c-2) or (c-4) and/or (b) R$^2$ is an optionally substituted imidazolyl or pyridyl group, then R$^7$ is not oxygen or sulphur.

As used in the foregoing definitions and hereinafter, halo is generic to fluoro, chloro, bromo and iodo; C$_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; C$_{1-6}$alkyl includes C$_{1-4}$alkyl and the higher homologues thereof having 5 to 6 carbon atoms such as, for example, pentyl, 2-methylbutyl, hexyl, 2-methylpentyl and the like; C$_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; haloC$_{1-6}$alkyl defines C$_{1-6}$alkyl containing one or more halo substituents for example trifluoromethyl; C$_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like. The term "S(O)" refers to a sulfoxide and "S(O)$_2$" to a sulfone. Aryl defines phenyl, naphthalenyl or phenyl substituted with one or more substituents each independently selected from halo, C$_{1-6}$alkyl, C$_{1-6}$alkyloxy or trifluoromethyl, cyano, hydroxycarbonyl.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable acid addition salts and all stereoisomeric forms.

Examples of compounds of formula (I) include those wherein one or more of the following restrictions apply:

r is 0, 1 or 2;
t is 0 or 1;
>$Y^1$—$Y^2$— is a trivalent radical of formula

| >C=N— | (y-1) |
| >C=CR$^9$— | (y-2) | wherein $R^9$ is hydrogen, cyano, halo, $C_{1-6}$alkyl, hydroxy$C_{1-6}$alkyl, hydroxycarbonyl or aminocarbonyl;

$R^1$ is halo, $C_{1-6}$alkyl, —$(CR^{20}R^{21})_p$—$C_{3-10}$cycloalkyl, trihalomethyl, trihalomethoxy, $C_{2-6}$alkenyl, hydroxycarbonyl$C_{2-6}$alkenyl, $C_{2-6}$alkynyl, $C_{1-6}$alkyloxy, hydroxy$C_{1-6}$alkyloxy, amino$C_{1-6}$alkyloxy, $C_{1-6}$alkylthio, hydroxycarbonyl, $C_{1-6}$alkyloxycarbonyl, —$CONR^{22}R^{23}$, or —CH=NOR$^{25}$; or two $R^1$ substituents adjacent to one another on the phenyl ring may independently form together a bivalent radical of formula

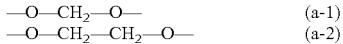

| —O—CH$_2$—O— | (a-1) |
| —O—CH$_2$—CH$_2$—O— | (a-2) |

$R^2$ is a 5- or 6-membered monocyclic heterocyclic ring containing one, two or three heteroatoms selected from oxygen, sulphur or nitrogen or a 9- or 10-membered bicyclic heterocyclic ring $R^3$ is hydrogen, $C_{1-6}$alkyl, —$(CR^{20}R^{21})_p$—$C_{3-10}$cycloalkyl, halo$C_{1-6}$alkyl, cyano$C_{1-6}$alkyl, hydroxy$C_{1-6}$alkyl, $C_{1-6}$alkyloxy$C_{1-6}$alkyl, —$C_{1-6}$alkyl $NR^{22}R^{23}$, Het$^2C_{1-6}$alkyl, —$C_{2-6}$alkenyl $NR^{22}R^{23}$, or -Het$^2$; or a group of formula

| —O—R$^{10}$ | (b-1) |
| —NR$^{11}$R$^{12}$ | (b-3) | wherein $R^{10}$ is hydrogen, $C_{1-6}$alkyl, or —$(CR^{20}R^{21})_p$—$C_{3-10}$cycloalkyl, or a group of formula -Alk-OR$^{13}$ or -Alk-NR$^{14}$R$^{15}$;

$R^{11}$ is hydrogen or $C_{1-6}$alkyl;

$R^{12}$ is hydrogen, hydroxy, $C_{1-6}$alkyl, —$(CR^{20}R^{21})_p$—$C_{3-10}$cycloalkyl, $C_{1-6}$alkyloxy, $C_{1-6}$alkylcarbonyl, aminocarbonyl, or a radical of formula -Alk-OR$^{13}$ or Alk-NR$^{14}$R$^{15}$;

wherein Alk is $C_{1-6}$alkanediyl;

$R^{13}$ is hydrogen, $C_{1-6}$alkyl or —$(CR^{20}R^{21})_p$—$C_{3-10}$cycloalkyl;

$R^{14}$ is hydrogen, $C_{1-6}$alkyl, or —$(CR^{20}R^{21})_p$—$C_{3-10}$cycloalkyl;

$R^{15}$ is hydrogen or $C_{1-6}$alkyl;

$R^4$ is a radical of formula (c-2) or (c-3)

wherein $R^{16}$ is hydrogen, halo or $C_{1-6}$alkyl, $R^{17}$ is hydrogen, $C_{1-6}$alkyl, —$(CR^{20}R^{21})_p$—$C_{3-10}$cycloalkyl, $C_{1-6}$alkyloxy$C_{1-6}$alkyl or trifluoromethyl;

$R^{18}$ is hydrogen, $C_{1-6}$alkyl or —$(CR^{20}R^{21})_p$—$C_{3-10}$cycloalkyl;

$R^{18a}$ is hydrogen;

$R^5$ is cyano, halo, $C_{1-6}$alkyl, $C_{2-6}$alkynyl, $C_{1-6}$alkyloxy or $C_{1-6}$alkyloxycarbonyl:

$R^6$ is hydrogen, $C_{1-6}$alkyl, —$C_{1-6}$alkylCO$_2$R$^{24}$, —$C_{1-6}$alkylC(O)NR$^{22}$R$^{23}$, -Alk-Ar$^2$, -AlkHet$^2$ or —$(CR^{20}R^{21})_p$—$C_{3-10}$cycloalkyl, $R^7$ is oxygen; or $R^6$ and $R^7$ together form a trivalent radical of formula (x-1), (x-2), (x-3), (x-4) or (x-9)

Het$^2$ is a 5- or 6-membered monocyclic heterocyclic ring containing one, two or three heteroatoms selected from oxygen, sulphur or nitrogen for example pyrrolidinyl, imidazolyl, triazolyl, tetrazolyl, pyridyl, pyrimidinyl, furyl, morpholinyl, piperazinyl, piperidinyl, thiophenyl, thiazolyl or oxazolyl, or a 9- or 10-membered bicyclic heterocyclic ring especially one in which a benzene ring is fused to a heterocyclic ring containing one, two or three heteroatoms selected from oxygen, sulphur or nitrogen for example indolyl, benzofuryl, benzothienyl, quinolinyl, benzimidazolyl, benzotriazolyl, benzoxazolyl, benzothiazolyl or benzodioxolanyl.

A group of interesting compounds consists of those compounds of formula (I) wherein one or more of the following restrictions apply:

>$Y^1$—$Y^2$— is a trivalent radical of formula (y-1) or (y-2), wherein $R^9$ is hydrogen, halo, $C_{1-4}$alkyl, hydroxycarbonyl, or $C_{1-4}$alkyloxycarbonyl;

r is 0, 1 or 2;

t is 0;

$R^1$ is halo, $C_{1-6}$alkyl or two $R^1$ substituents ortho to one another on the phenyl ring may independently form together a bivalent radical of formula (a-1);

$R^2$ is a 5- or 6-membered monocyclic heterocyclic ring containing one or two heteroatoms selected from oxygen, sulphur or nitrogen or a 9- or 10-membered bicyclic heterocyclic ring in which a benzene ring is fused to a heterocyclic ring containing one, two or three heteroatoms selected from oxygen, sulphur or nitrogen, optionally substituted by halo, cyano, $C_{1-6}$alkyl or aryl; $R^3$ is Het$^2$ or a group of formula (b-1) or (b-3) wherein $R^{10}$ is hydrogen or a group of formula -Alk-OR$^{13}$.

$R^{11}$ is hydrogen;

$R^{12}$ is hydrogen, $C_{1-6}$alkyl, $C_{1-6}$alkylcarbonyl, hydroxy, $C_{1-6}$alkyloxy or mono- or di($C_{1-6}$alkyl)amino$C_{1-6}$alkylcarbonyl;

Alk is $C_{1-6}$alkanediyl and $R^{13}$ is hydrogen;

$R^4$ is a group of formula (c-2) or (c-3) wherein $R^{16}$ is hydrogen, halo or mono- or di($C_{1-4}$alkyl)amino;

$R^{17}$ is hydrogen or $C_{1-6}$alkyl;

$R^{18}$ is hydrogen or $C_{1-6}$alkyl;

$R^{18a}$ is hydrogen;

$R^6$ is —$(CR^{20}R^{21})_p$—$C_{3-10}$cycloalkyl, —$C_{1-6}$alkylCO$_2$R$^{24}$, aminocarbonyl$C_{1-6}$alkyl, -Alk-Ar$^2$ or -AlkHet$^2$ or $C_{1-6}$alkyl;

$R^7$ is oxygen; or $R^6$ and $R^7$ together form a trivalent radical of formula (x-1), (x-2), (x-3), (x-4) or (x-9)

aryl is phenyl.

A particular group of compounds consists of those compounds of formula (I) wherein >$Y^1$—$Y^2$ is a trivalent radical of formula (y-1) or (y-2), r is 0 or 1, t is 0, $R^1$ is halo, $C_{(1-4)}$alkyl or forms a bivalent radical of formula (a-1), $R^2$ is a 5- or 6-membered monocyclic heterocyclic ring containing one or two heteroatoms selected from oxygen, sulphur or nitrogen or a 9- or 10-membered bicyclic heterocyclic ring in which a benzene ring is fused to a heterocyclic ring containing one or two heteroatoms selected from oxygen, sulphur or nitrogen, optionally substituted by halo, cyano, $C_{1-6}$alkyl or aryl.

R³ is hydrogen or a radical of formula (b-1) or (b-3), R¹⁰ is hydrogen or -Alk-OR¹³, R¹¹ is hydrogen and R¹² is hydrogen or $C_{1-6}$alkylcarbonyl and R¹³ is hydrogen; R⁴ is a radical of formula (c-2) or (c-3), wherein R¹⁶ is hydrogen, R¹⁷ is $C_{1-6}$alkyl, R¹⁸ is $C_{1-6}$alkyl, R¹⁸ᵃ is hydrogen;
R⁶ is $C_{1-6}$alkyl, —CH₂—$C_{3-10}$cycloalkyl, —$C_{1-6}$alkylCO₂R²⁴ (R²⁴=H, Et), aminocarbonyl$C_{1-6}$alkyl, -Alk-Ar² or -AlkHet²; and
R⁷ is oxygen; or R⁶ and R⁷ together form a trivalent radical of formula (x-2), (x-3) or (x-4).

More preferred compounds are those compounds of formula (I) wherein >Y¹—Y² is a trivalent radical of formula (y-1) or (y-2), r is 0 or 1, s is 1, t is 0, R¹ is halo, preferably chloro and most preferably 3-chloro, R² is a thiophene, furyl, pyridyl, diazolyl, oxazolyl, benzodiazolyl, benzotriazolyl, or quinolinyl group, optionally substituted by halo preferably chloro, cyano, $C_{1-6}$alkyl, preferably methyl, or aryl; R³ is hydrogen or a radical of formula (b-1) or (b-3), R⁹ is hydrogen, R¹⁰ is hydrogen, R¹¹ is hydrogen and R¹² is hydrogen; R⁴ is a radical of formula (c-2) or (c-3), wherein R¹⁶ is hydrogen, R¹⁷ is $C_{1-6}$alkyl, R¹⁸ is $C_{1-6}$alkyl, R¹⁸ᵃ is hydrogen; R⁶ is $C_{1-6}$alkyl, —CH₂—$CH_{3-10}$cycloalkyl or —$C_{1-6}$alkylAr²;
R⁷ is oxygen; or R⁶ and R⁷ together form a trivalent radical of formula (x-2) or (x-4).

Especially preferred compounds are those compounds of formula (I) wherein >Y¹—Y² is a trivalent radical of formula (y-1) or (y-2), r is 1, s is 0, R¹ is halo, preferably chloro, and most preferably 3-chloro, R² is a 4-chloro-thiophen-2-yl, 3-furyl, 5-chloro-pyrid-3-yl, 2-phenyl-imidazol-1-yl, 2-ethyl-imidazol-1-yl, benzimidazol-1-yl or 2-hydroxyquinoline-7-yl group; R³ is a radical of formula (b-1) or (b-3), R⁹ is hydrogen, R¹⁰ and R¹¹ are hydrogen and R¹² is hydrogen or hydroxy; R⁴ is a radical of formula (c-2) or (c-3), wherein R¹⁶ is hydrogen, R¹⁷ is $C_{1-6}$alkyl preferably methyl, R¹⁸ is $C_{1-6}$alkyl preferably methyl, R¹⁸ᵃ is hydrogen; R⁶ is $C_{1-6}$alkyl, —CH₂—$C_{3-10}$cycloalkyl or -alkylAr²; R⁷ is oxygen; or R⁶ and R⁷ together form a trivalent radical of formula (x-4).

The most preferred compounds according to the invention are:

5-(3-chlorophenyl)-α-(5-chloro-2-thienyl)-α-(1-methyl-1H-imidazol-5-yl)-tetrazolo[1,5-a]quinazoline-7-methanol,
5-(3-chlorophenyl)-α-(5-chloro-2-thienyl)-α-(1-methyl-1H-imidazol-5-yl)-tetrazolo[1,5-a]quinoline-7-methanol,
5-(3-chlorophenyl)-α-(3-furanyl)-α-(1-methyl-1H-imidazol-5-yl)-tetrazolo[1,5-a]quinoline-7-methanol,
5-(3-chlorophenyl)-α-(3-furanyl)-α-(1-methyl-1H-imidazol-5-yl)-tetrazolo[1,5-a]quinazoline-7-methanol,
5-(3-chlorophenyl)-α-(1-methyl-1H-imidazol-5-yl)-α-(6-quinolinyl)-tetrazolo[1,5-a]quinazoline-7-methanol,
4-(3-chlorophenyl)-6-[(5-chloro-2-thienyl)hydroxy(4-methyl-4H-1,2,4-triazol-3-yl)methyl]-1-methyl-2(1H)-quinolinone,
5-(3-chlorophenyl)-α-(6-chloro-3-pyridinyl)-α-(1-methyl-1H-imidazol-5-yl)-tetrazolo[1,5-a]quinoline-7-methanol,
5-(3-chlorophenyl)-α-(3-furanyl)-α-(1-methyl-1H-imidazol-5-yl)-tetrazolo[1,5-a]quinoline-7-methanamine,
5-(3-chlorophenyl)-α-(5-chloro-2-thienyl)-α-(1-methyl-1H-imidazol-5-yl)-tetrazolo[1,5-a]quinoline-7-methanamine,
5-(3-chlorophenyl)-α-(5-chloro-2-thienyl)-α-(1-methyl-1H-imidazol-5-yl)-tetrazolo[1,5-a]quinazoline-7-methanamine,
α-(2-benzofuranyl)-5-(3-chlorophenyl)-α-(1-methyl-1H-imidazol-5-yl)-tetrazolo[1,5-a]quinoline-7-methanamine,
5-(3-chlorophenyl)-α-(6-chloro-3-pyridinyl)-α-(1-methyl-1H-imidazol-5-yl)-tetrazolo[1,5-a]quinoline-7-methanamine,
4-(3-chlorophenyl)-6-[(5-chloro-2-thienyl)hydroxy(1-methyl-1H-imidazol-5-yl)methyl]-1-methyl-2(1H)-quinazolinone,
5-(3-chlorophenyl)-α-(1-methyl-1H-imidazol-5-yl)-α-(5-methyl-2-thienyl)-tetrazolo[1,5-a]quinoline-7-methanol,
5-(3-chlorophenyl)-7-[(1-methyl-1H-imidazol-5-yl)(2-phenyl-1H-imidazol-1-yl)methyl]-tetrazolo[1,5-a]quinazoline,
α-(2-benzofuranyl)-5-(3-chlorophenyl)-α-(1-methyl-1H-imidazol-5-yl)-tetrazolo[1,5-a]quinazoline-7-methanamine,
5-(3-chlorophenyl)-7-[(2-ethyl-1H-imidazol-1-yl)(1-methyl-1H-imidazol-5-yl)methyl]-tetrazolo[1,5-a]quinazoline,
5-(3-chlorophenyl)-α,α-bis(1-methyl-1H-imidazol-5-yl)-tetrazolo[1,5-a]quinazoline-7-methanol,
5-(3-chlorophenyl)-7-[[2-(4-fluorophenyl)-1H-imidazol-1-yl](1-methyl-1H-imidazol-5-yl)methyl]-tetrazolo[1,5-a]quinazoline,
α-benzo[b]thien-2-yl-5-(3-chlorophenyl)-α-(1-methyl-1H-imidazol-5-yl)-tetrazolo[1,5-a]quinoline-7-methanamine,
5-(3-chlorophenyl)-7-[(1-methyl-1H-imidazol-5-yl)(2-phenyl-1H-imidazol-1-yl)-methyl]-tetrazolo[1,5-a]quinoline,
5-(3-chlorophenyl)-7-[[2-(2-chlorophenyl)-1H-imidazol-1-yl](1-methyl-1H-imidazol-5-yl)methyl]-tetrazolo[1,5-a]quinoline,
3-[1-[[5-(3-chlorophenyl)tetrazolo[1,5-a]quinazolin-7-yl](1-methyl-1H-imidazol-5-yl)methyl]-1H-imidazol-2-yl]-benzonitrile,
5-(3-chlorophenyl)-7-[(2-ethyl-1H-imidazol-1-yl)(1-methyl-1H-imidazol-5-yl)methyl]-tetrazolo[1,5-a]quinoline, and their pharmaceutically acceptable salts.

The compounds of formula (I) and their pharmaceutically acceptable salts and N-oxides and stereochemically isomeric forms thereof may be prepared in conventional manner, for example by a process which comprises:

a) cyclising a compound of formula (II)

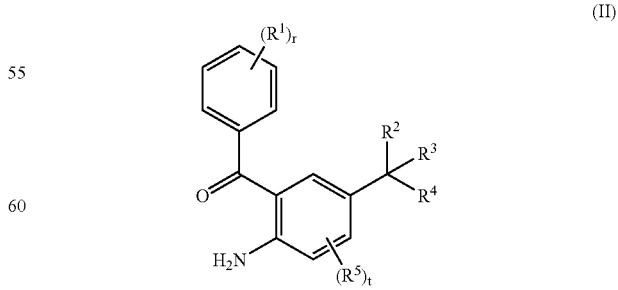

with a reagent serving to form a compound of formula (I) in which R⁶ is hydrogen and R⁷ is oxygen;

b) reacting a compound of formula (III):

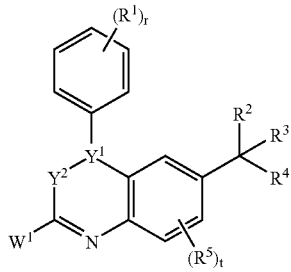

in which $W^1$ represents a replaceable or reactive group, with a reagent serving either to react with or replace the $W^1$ group in compound (III) to form a compound of formula (I) in which $R^6$ is hydrogen and $R^7$ is an oxygen or sulphur group or to react with the $W^1$ group and the adjacent nitrogen atom to form directly or indirectly a compound of formula (I) in which $R^6$ and $R^7$ together form a trivalent radical selected from formulae (x-1) to (x-10); or c) reacting a compound of formula (IV):

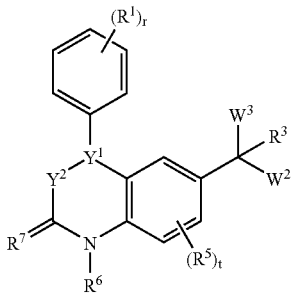

in which $W^2$ is a leaving group and $W^3$ is the group $R^2$ above or $W^2$ is the group $R^4$ above and $W^3$ is a leaving group, with a reagent serving to replace the leaving group $W^2$ or $W^3$ with the respective $R^4$ or $R^2$ group; or d) reacting a compound of formula (V):

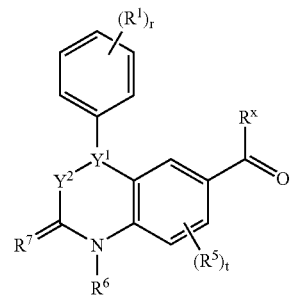

(in which $R^x$ is the group $R^2$ or $R^4$ above) with a heterocyclic reagent of formula $R^{4a}L$ (when $R^x$ is $R^2$) or $R^{2a}L$ (when $R^x$ is $R^4$) in which L is a leaving atom or group and $R^{2a}$ is $R^2$ or a precursor group therefor and $R^{4a}$ is $R^4$ or a precursor group therefor, and if required, converting said precursor group to the parent group, to form a compound of formula (I) in which $R^3$ is hydroxy;

e) reacting a compound of formula (VI):

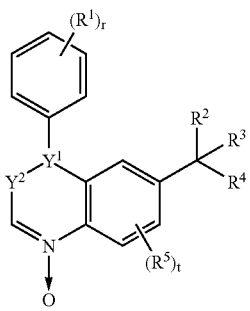

with a reagent serving to convert the said compound (VI) to a compound of formula (I) in which $R^6$ is hydrogen and $R^7$ is oxygen;

and optionally effecting one or more of the following conversions in any desired order:
(i) converting a compound of formula (I) into a different compound of formula (I);
(ii) converting a compound of formula (I) in to a pharmaceutically acceptable salt or N-oxide thereof;
(iii) converting a pharmaceutically acceptable salt or N-oxide of a compound of formula (I) into the parent compound of formula (I);
(iv) preparing a stereochemical isomeric form of a compound of formula (I) or a pharmaceutically acceptable salt or N-oxide thereof.

With regard to process a), this can be effected as described for example in an analogous manner to that described in WO 97/21701 and WO98/49157 referred to above. Thus, the cyclisation may be effected for example by subjecting the compound of formula (II) to an acetylation reaction, e.g. by treatment with the anhydride of a carboxylic acid, e.g. acetic anhydride in a reaction-inert solvent, e.g. toluene, and subsequent reaction with a base such as potassium tert-butoxide in a reaction-inert solvent such as 1,2-dimethoxyethane.

With regard to process b), this can also be effected for example in an analogous manner to that as described in WO 97/21701 and WO98/49157 referred to above for the preparation of compounds in which $R^7$ is oxygen, for example by hydrolysis of an ether of formula (III) in which $W^1$ is $C_{1-6}$alkyloxy in an aqueous acid solution such hydrochloric acid. Alternatively a compound of formula (III) in which $W^1$ is a chloro radical can be used.

Also with regard to process b), for the preparation of compounds in which $R^6$ and $R^7$ together form a trivalent radical of formula (x-1) to (x-10), this can be effected as described for example in WO 00/39082 referred to above. For example, when $W^1$ is chloro, the compound of formula (III) can be reacted with an azide compound for example sodium azide to form a corresponding compound of formula (I) in which $R^6$ and $R^7$ together form a trivalent radical of formula (x-4). Alternatively, when $W^1$ is chloro, the compound of formula (III) can be reacted with aquous hydrazine to form a compound of formula (III) where $W^1$ is $NHNH_2$ which by reaction with sodium nitrite in acidic media form a corresponding compound of formula (I) in which $R^6$ and $R^7$ together form a trivalent radical of formula (x-4).

With regard to process c), this can be effected for example by N-alkylating an intermediate of formula (IVa), wherein $W^2$ is an appropriate leaving group such as, for example, chloro, bromo, methanesulfonyloxy or benzenesulfonyloxy, with an intermediate of formula (VII) to form a a compound of formula (I) in which $R^4$ is a group of formula (c-1) represented by compounds of formula (I-a):

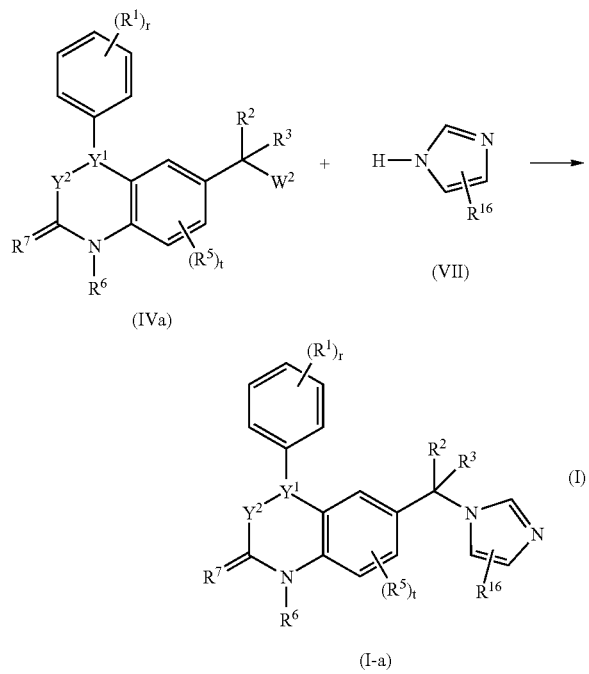

The reaction can be performed in a reaction-inert solvent such as, for example, acetonitrile, and optionally in the presence of a suitable base such as, for example, sodium carbonate, potassium carbonate or triethylamine. Stirring may enhance the rate of the reaction. The reaction may conveniently be carried out at a temperature ranging between room temperature and reflux temperature.

Also, compounds of formula (I-a) can be prepared by reacting an intermediate of formula (IVb) in which $W^2$ is hydroxy with an intermediate of formula (VIII), wherein Y is oxygen or sulfur, such as, for example, a 1,1'-carbonyldiimidazole.

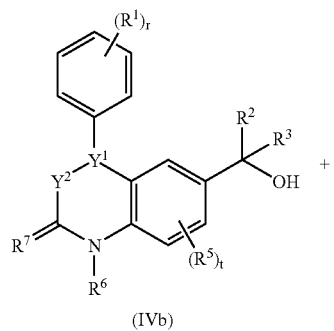

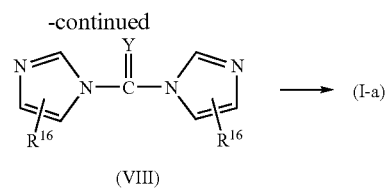

Said reaction may conveniently be conducted in a reaction-inert solvent, such as, e.g. tetrahydrofuran, optionally in the presence of a base, such as sodium hydride, and at a temperature ranging between room temperature and the reflux temperature of the reaction mixture.

Similar procedures can be used to introduce the $R^2$ group using a compound of formula (IV) in which $W^3$ is a leaving group.

With regard to process d), this can be used to introduce the $R^4$ group, for example by reacting a compound of formula (V) in which $R^x$ is $R^2$ with an imidazole reagent to form a compound of formula (I) in which $R^4$ is a group of formula (c-2), or with a 3-mercapto-4-$C_{1-6}$alkyl-1,2,4-triazole reagent to form the corresponding 3-mercapto-4-$C_{1-6}$alkyl-1,2,4-triazole derivative, which is optionally methylated to form the corresponding 3-methylmercapto derivative, and subsequently removing the 3-mercapto or 3-methylmercapto group to form a compound of formula(I) in which $R^4$ is a group of formula (c-3) in which $R^{18}$ is a $C_{1-6}$alkyl group; or with a 3-bromopyridyl group to form a compound of formula (I) in which $R^4$ is a group of formula (c-4). In more detail, the compounds of formula (I) wherein $R^4$ represents a radical of formula (c-2), $R^3$ is hydroxy and $R^{17}$ is $C_{1-6}$alkyl, said compounds being referred to as compounds of formula (I-b-1) may be prepared by reacting an intermediate ketone of formula (Va) with an intermediate of formula (III-1). Said reaction requires the presence of a suitable strong base, such as, for example, butyl lithium in an appropriate solvent, such as, for example, tetrahydrofuran, and the presence of an appropriate silane derivative, such as, for example, triethylchlorosilane. During the work-up procedure an intermediate silane derivative is hydrolyzed. Other procedures with protective groups analogous to silane derivatives can also be applied.

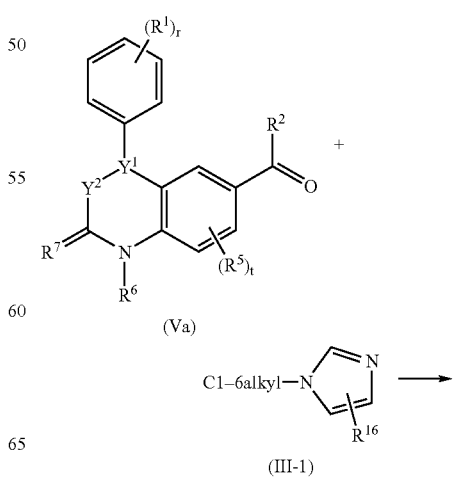

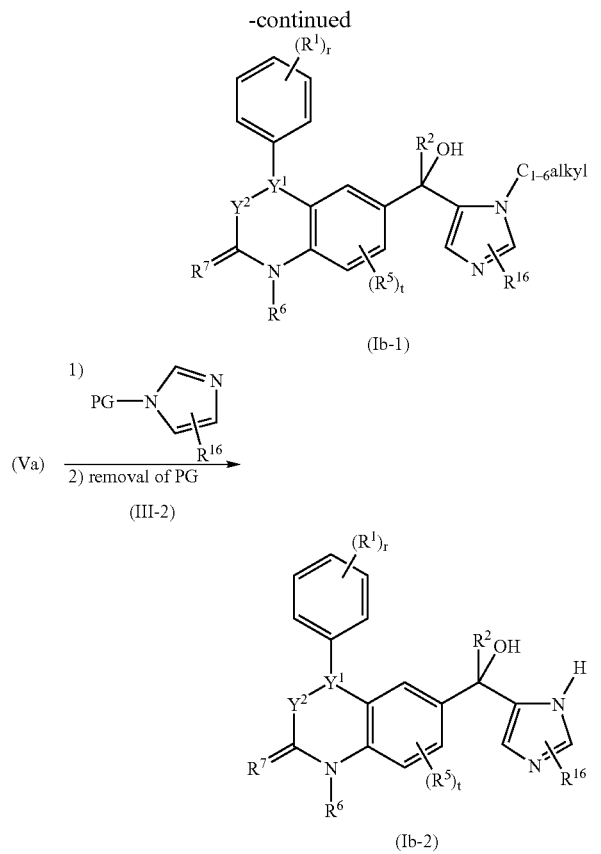

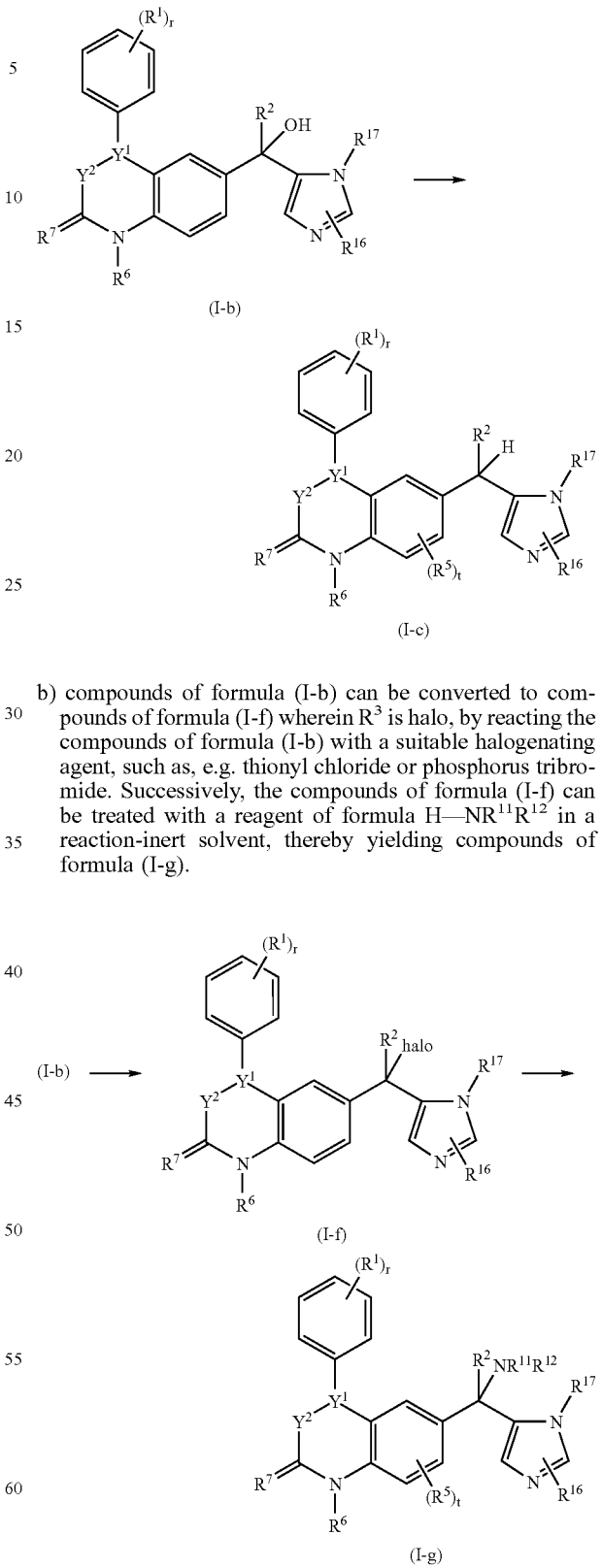

Also, the compounds of formula (I), wherein $R^4$ is a radical of formula (c-2), $R^3$ is hydroxy and $R^{17}$ is hydrogen, said compounds being referred to as compounds of formula (I-b-2) may be prepared by reacting an intermediate ketone of formula (Va) with a intermediate of formula (III-2), wherein PG is a protective group such as, for example, a sulfonyl group, e.g. a dimethylamino sulfonyl group, which can be removed after the addition reaction. Said reaction is conducted analogously as for the preparation of compounds of formula (I-b-1), followed by removal of the protecting group PG, yielding compounds of formula (I-b-2). Similar procedures can be used to introduce the $R^2$ group by reacting a compound of formula (V) in which $R^x$ is $R^4$ with a $R^2L$ reagent for example a lithium compound.

With regard to process e), this may be effected for example as described in WO 97/21701 referred to above, by reacting the nitrone of formula (VI) with the anhydride of a carboxylic acid, e.g. acetic anhydride, thus forming the corresponding ester on the 2-position of the quinoline moiety, which ester can then be hydrolysed in situ to the corresponding quinolinone using a base such potassium carbonate.

Examples of the interconversion of one compound of formula (I) into a different compound of formula (I) include the following reactions:

a) compounds of formula (I-b) can be converted to compounds of formula (I-c), defined as a compound of formula (I) wherein $R^4$ is a radical of formula (c-2) and $R^3$ is hydrogen, by submitting the compounds of formula (I-b) to appropriate reducing conditions, such as, e.g. stirring in acetic acid in the presence of formamide, or treatment with sodium borohydride/trifluoroacetic acid.

b) compounds of formula (I-b) can be converted to compounds of formula (I-f) wherein $R^3$ is halo, by reacting the compounds of formula (I-b) with a suitable halogenating agent, such as, e.g. thionyl chloride or phosphorus tribromide. Successively, the compounds of formula (I-f) can be treated with a reagent of formula H—$NR^{11}R^{12}$ in a reaction-inert solvent, thereby yielding compounds of formula (I-g).

c) compounds of formula (I-b) can be converted into compounds of formula (I-g) for example by treatment with $SOCl_2$, and then $NH_3$/iPrOH, e.g. in a tetrahydrofuran solvent, or by treatment with acetic acid ammonium salt at a temperature ranging from 120 to 180° C., or by treatment with sulfamide at a temperature ranging from 120 to 180° C.;

d) compounds of formula (I-f) can be converted into compounds of formula (I-c) for example by treatment with $SnCl_2$ in the presence of concentrated HCl in acetic acid at reflux;

e) compounds of formula (I) in which $>Y^1$—$Y^2$ represents a radical of formula (y-1) or (y-2) can be convened into corresponding compounds of formula (I) in which $>Y^1$—$Y^2$ represents a radical of formula (y-3) or (y-4) respectively, by conventional reduction procedures for example hydrogenation or reduction by treatment with sodium borohydride in a suitable solvent, e.g. methanol, and vice versa by conventional oxidation procedures, e.g. oxidation with $MnO_2$ in a reaction-inert solvent, e.g. dichloromethane;

f) compounds of formula (I) in which X is oxygen can be converted into corresponding compounds of formula (I) in which X is sulphur with a reagent such as phosphorus pentasulfide or Lawesson's reagent in a suitable solvent such as, for example, pyridine.

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond.

The intermediates and starting materials used in the above-described processes may be prepared in conventional manner using procedures known in the art for example as described in the above-mentioned patent specifications WO 97/16443, WO 97/21701, WO 98/40383, WO 98/49157 and WO 00/39082.

Compounds of formula (III) in which $W^1$ is chloro, $R^3$ is hydroxy and $Y^1$—$Y^2$ is (y-1), herein referred to as compounds of formula (IIIa), may be prepared for example by procedures summarised in the following synthetic Routes A, B, C and D:

Route A

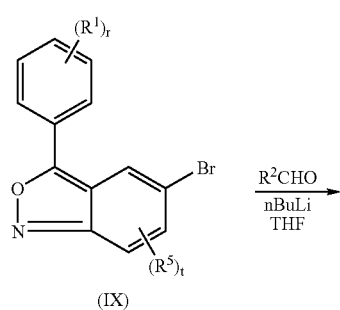

(IX)

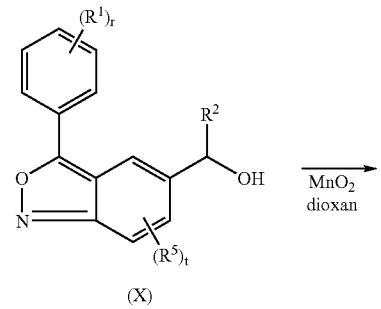

(X)

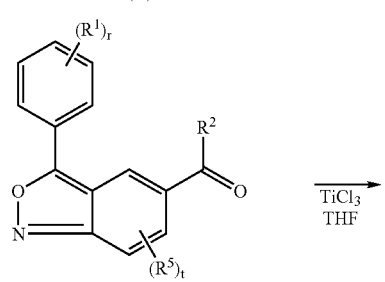

(XI)

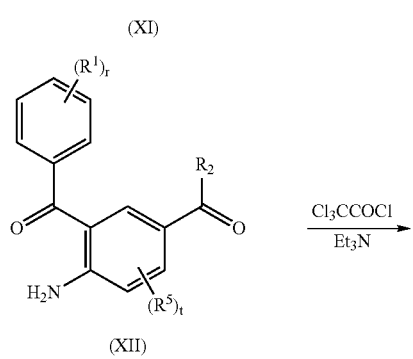

(XII)

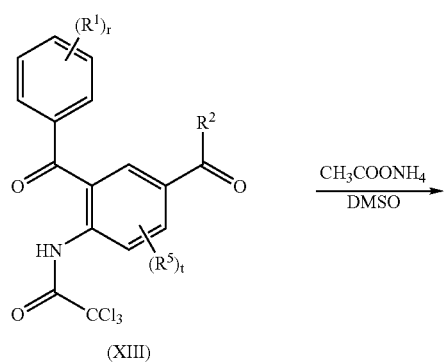

(XIII)

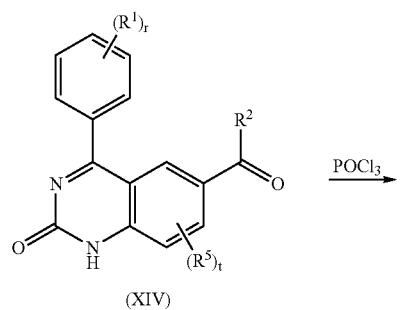

(XIV)

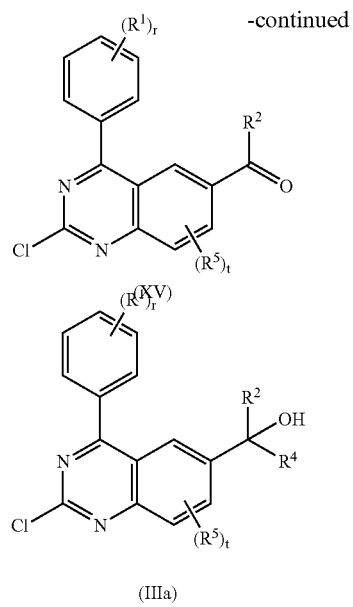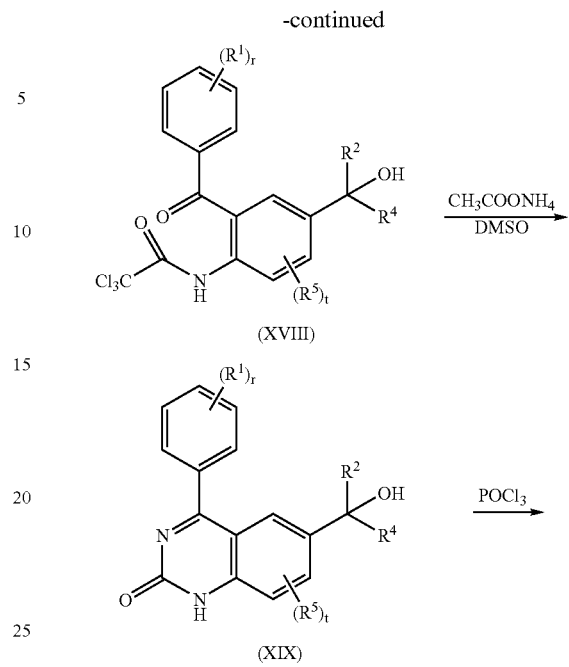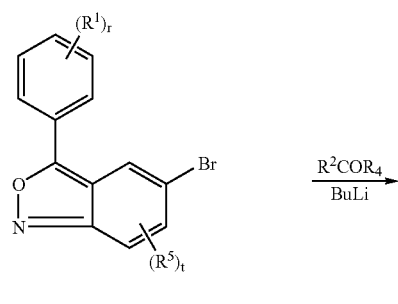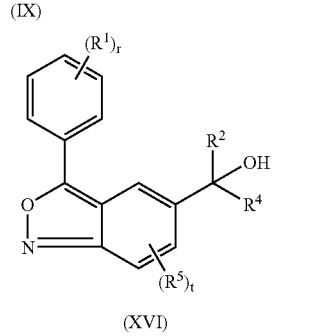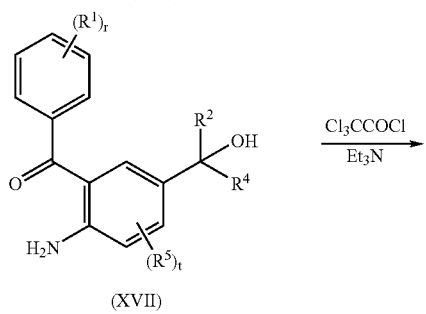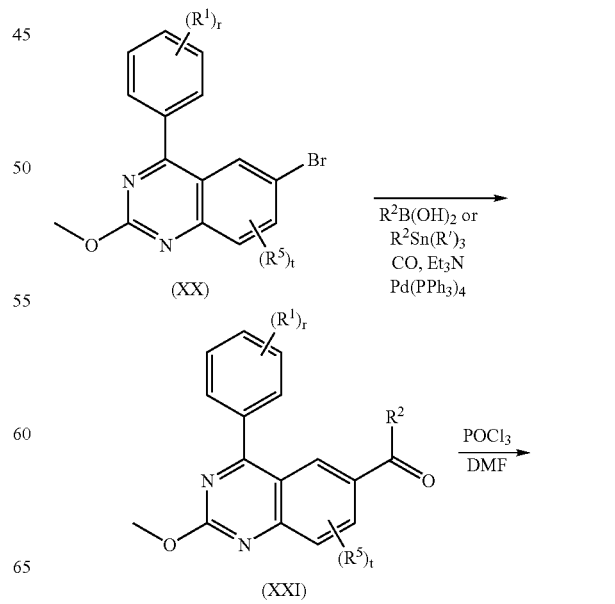
Route B
Route C

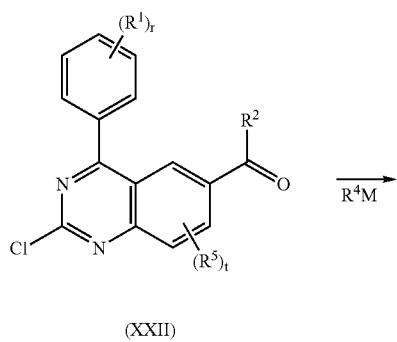
(XXII)
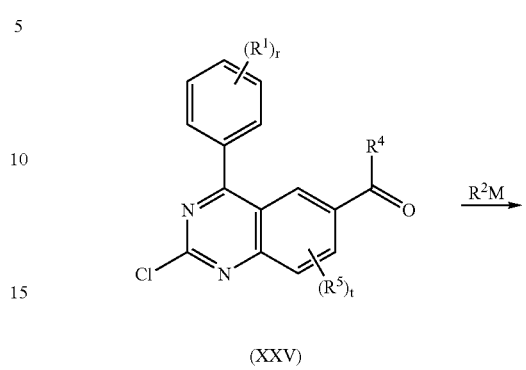
(XXV)
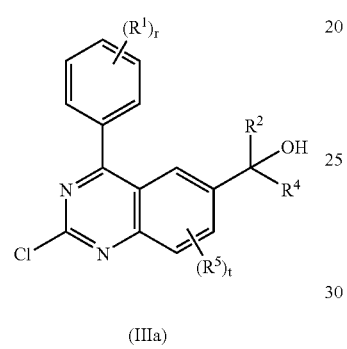
(IIIa)
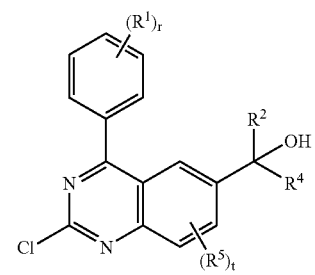
(IIIa)
Compounds of formula (III) in which $W^1$ is chloro, $R^3$ is hydroxy and $Y^1$—$Y^2$ is (y-2), herein referred to as compounds of formula (IIIb), may be prepared for example by procedures summarised in the following synthetic Routes E and F:
Route D
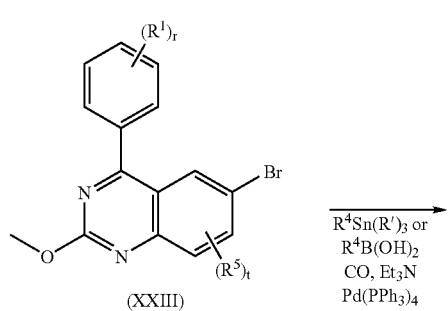
(XXIV)
Route E
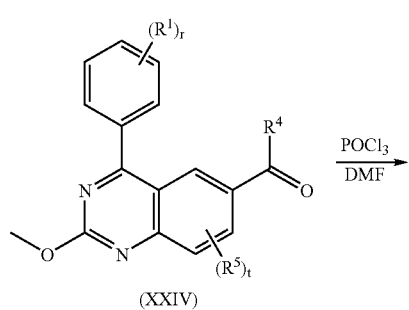
(XXX)
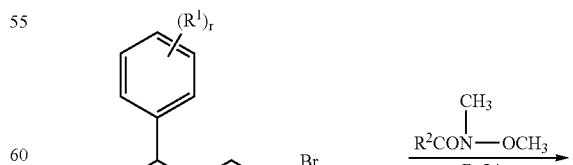

-continued
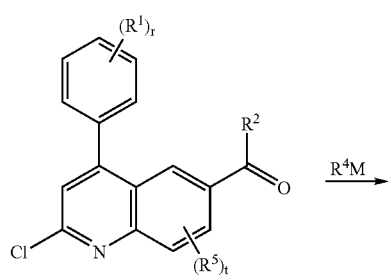
(XXXI)
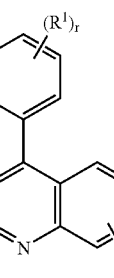
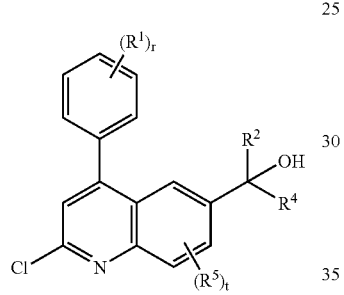
(IIIb)
Route F
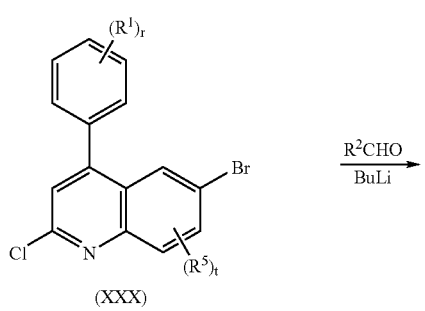
(XXX)
-continued
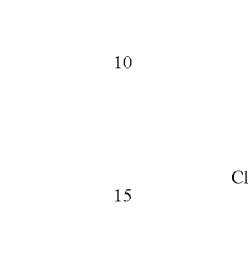
(XXXII)
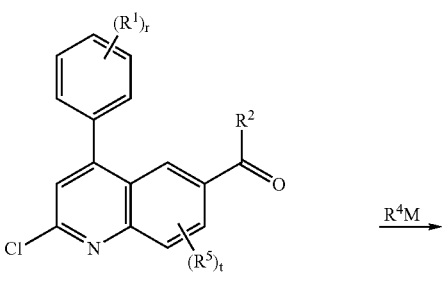
(XXXIII)
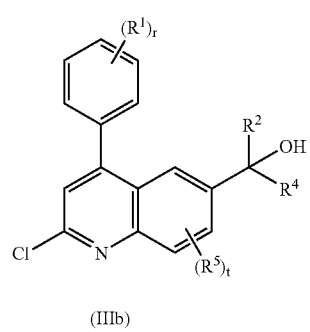
(IIIb)
Compounds of formula (IV) in which $W^3$ is chloro, $R^3$ is hydrogen, $Y^1—Y^2$ is (y-2) and $R^6$ and $R^7$ are (x-4), herein referred to as compounds of formula (IVa), may be prepared for example by procedures summarised in the following synthetic Routes G and H:

Route G
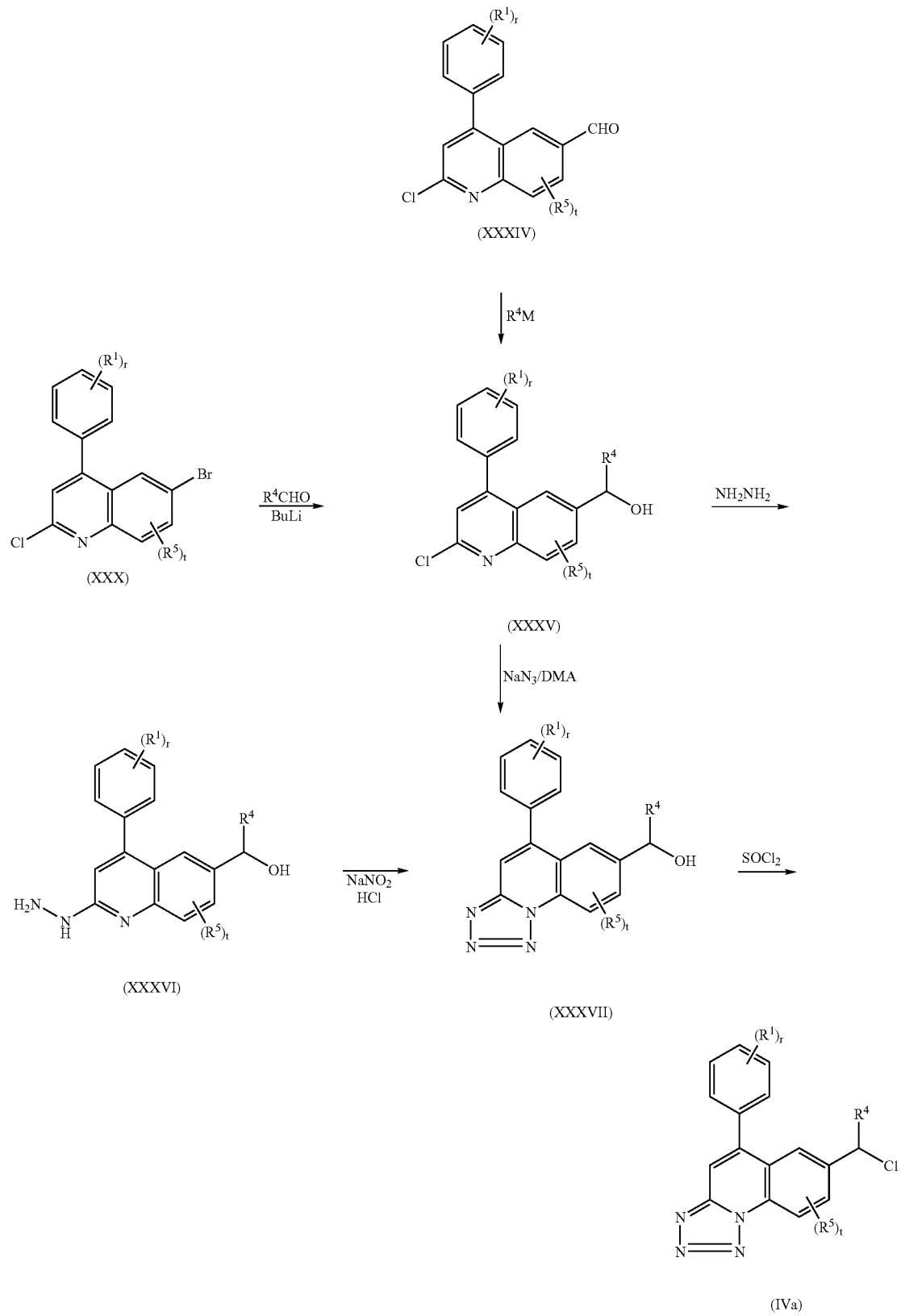

Route H
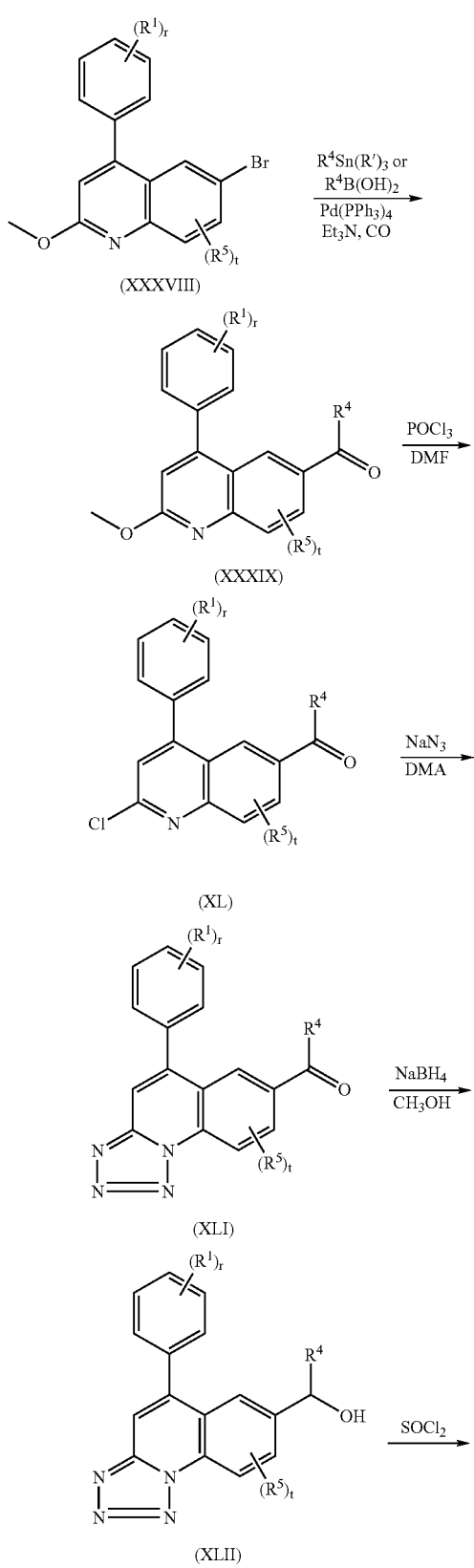
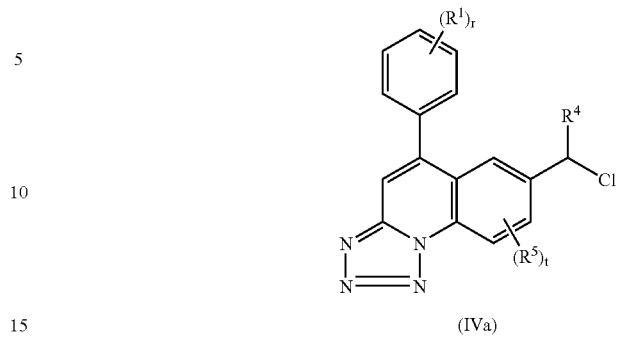
Compounds of formula (IV) in which $W^3$ is chloro, $R^3$ is hydrogen, $Y^1$—$Y^2$ is (y-1), $R^6$ and $R^7$ are (x-4), herein referred to as compounds of formula (IVb) may be prepared for example by procedures summarised in the following synthetic Route I:
Route I
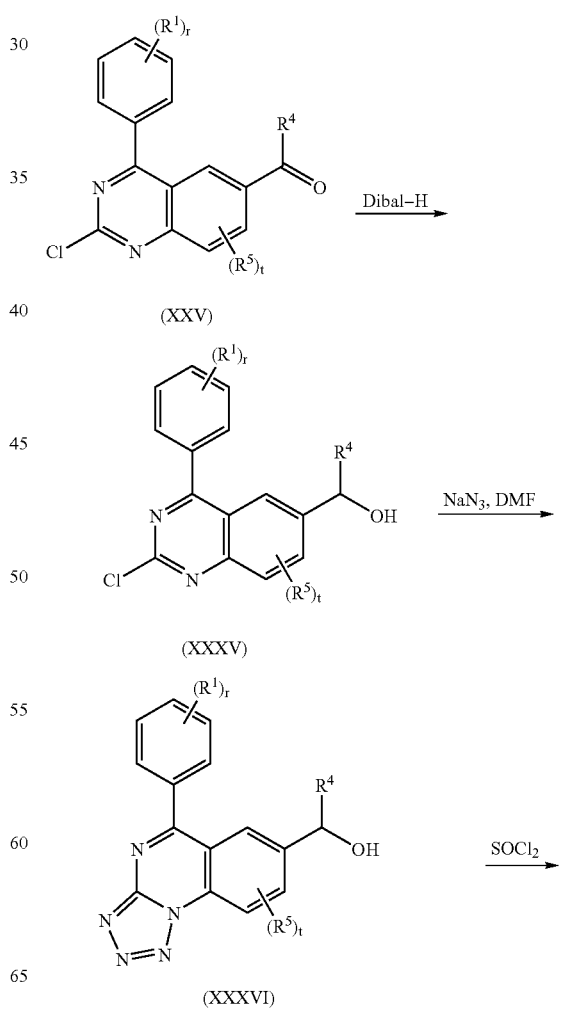

-continued

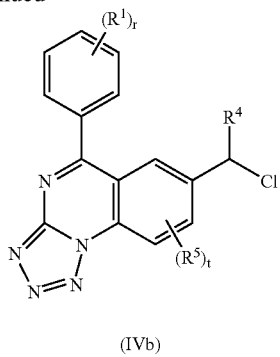

(IVb)

Compounds of formula (V) can be prepared in an analogous manner to the procedures described above for the preparation of other starting materials. For example certain of such compounds of formula (V) are prepared in the above described routes, for example compounds of formula (V) in which $Y^1$—$Y^2$ is (y-1), $R^6$ is hydrogen and $R^7$ is oxygen and $R^x$ is $R^2$ correspond to compounds of formula (XIV) in Route A, and compounds of formula (V) in which $Y^1$—$Y^2$ is (y-2) and $R^6$ and $R^7$ are (x-4) and correspond to compounds of formula (XXXVIII) in Route H.

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

This invention provides a method for inhibiting the abnormal growth of cells, including transformed cells, by administering an effective amount of a compound of the invention. Abnormal growth of cells refers to cell growth independent of normal is regulatory mechanisms (e.g. loss of contact inhibition). This includes the abnormal growth of: (1) tumor cells (tumors) expressing an activated ras oncogene; (2) tumor cells in which the rat protein is activated as a result of oncogenic mutation of another gene; (3) benign and malignant cells of other proliferative diseases in which aberrant ras activation occurs. Furthermore, it has been suggested in literature that ras oncogenes not only contribute to the growth of tumors in vivo by a direct effect on tumor cell growth but also indirectly, i.e. by facilitating tumor-induced angiogenesis (Rak. J. et al, *Cancer Research*, 55, 4575–4580, 1995). Hence, pharmacologically targeting mutant ras oncogenes could conceivably suppress solid tumor growth in vivo, in part, by inhibiting tumor-induced angiogenesis.

This invention also provides a method for inhibiting tumor growth by administering an effective amount of the compound of the invention to a subject, e.g. a mammal (and more particularly a human) in need of such treatment. In particular, this invention provides a method for inhibiting the growth of tumors expressing an activated ras oncogene by the administration of an effective amount of the compound of the invention. Examples of tumors which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), hematopoietic tumors of lymphoid lineage (e.g. acute lymphocytic leukemia, B-cell lymphoma, Burkitt's lymphoma), myeloid leukemias (for example, acute myclogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma (e.g. advanced breast cancer), kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes. With said inhibition being accomplished by the administration of an effective amount of the compounds described herein, to a subject in need of such a treatment. For example, the benign proliferative disorder neurofibromatosis, or tumors in which ras is activated due to mutation or overexpression of tyrosine kinase oncogenes, may be inhibited by the compounds of this invention.

The compound according to the invention can be used for other therapeutic purposes, for example:
  a) the sensitisation of tumors to radiotherapy by administering the compound according to the invention before, during or after irradiation of the tumor for treating cancer, for example as described in WO 00/01411;
  b) treating athropathies such as rheumatoid arthritis, osteoarthritis, juvenile arthritis, gout, polyarthritis, psoriatic arthritis, ankylosing spondylitis and systemic lupus erythematosus, for example as described in WO 00/1386;
  c) inhibiting smooth muscle cell proliferation including vascular proliferative disorders, atherosclerosis and restenosis, for example as described in WO 98/55124;
  d) treating inflammatory conditions such as ulcerative colitis, crohn's disease, allergic rhinitis, graft vs host disease, conjunctivitis, asthma, ards, behcets disease, transplant rejection, uticaria, allergic dermatitis, alopecia areata, scleroderma, exanthem, eczema, dermatomyositis, acne, diabetes, systemic lupus erythematosus, kawasaki's disease, multiple sclerosis, emphysema, cystic fibrosis and chronic bronchitis;
  e) treating endometriosis, uterine fibroids, dysfunctional uterine bleeding and endometrial hyperplasia;
  f) treating ocular vascularisation including vasculopathy affecting retinal and choroidal vessels;
  g) treating pathologies resulting from heterotrimeric G protein membrane fixation including diseases related to following biological functions or disorders; smell, taste, light, perception, neurotransmission, neurodegeneration, endocrine and exocrine gland functioning, autocrine and paracrine regulation, blood pressure, embryogenesis, viral infections, immunological functions, diabetes, obesity;

h) inhibiting viral morphogenesis for example by inhibiting the prenylation or the post-prenylation reactions of a viral protein such as the large delta antigen of hepatitis D virus; and the treatment of HIV infections;

i) treating polycystic kidney disease;

j) suppressing induction of inducible nitric oxide including nitric oxide or cytokine mediated disorders, septic shock, inhibiting apoptosis and inhibiting nitric oxide cytotoxicity;

k) treating malaria.

The compounds of present invention are particularly useful for the treatment of proliferative diseases, both benign and malignant, wherein the K-ras B isoform is activated as a result of oncogenic mutation.

Hence, the present invention discloses the compounds of formula (I) for use as a medicine as well as the use of these compounds of formula (I) for the manufacture of a medicament for treating one or more of the above-mentioned conditions.

For the treatment of the above conditions, the compound of the invention may be advantageously employed in combination with one or more other anti-cancer agents for example selected from platinum coordination compounds for example cisplatin or carboplatin, taxane compounds for example paclitaxel or docetaxel, camptothecin compounds for example irinotecan or topotecan, anti-tumor vinca alkaloids for example vinblastine, vincristine or vinorelbine, anti-tumor nucleoside derivatives for example 5-fluorouracil, gemcitabine or capecitabine, nitrogen mustard or nitrosourea alkylating agents for example cyclophosphamide, chlorambucil, carmustine or lomustine, anti-tumor anthracycline derivatives for example daunorubicin, doxorubicin or idarubicin; HER2 antibodies for example trastzumab; and anti-tumor podophyllotoxin derivatives for example etoposide or teniposide; and antiestrogen agents including estrogen receptor antagonists or selective estrogen receptor modulators preferably tamoxifen, or alternatively toremifene, droloxifene, faslodex and raloxifene, or aromatase inhibitors such as exemestane, anastrozole, letrazole and vorozole.

For the treatment of cancer the compounds according to the present invention can administered to a patient as described above in conjunction with irradiation; such treatment as may be especially beneficial as farnesyl transferase inhibitors can act as radiosensitisers for example as described in International Patent Specification WO 00/01411, enhancing the therapeutic effect of such irradiation.

Irradiation means ionizing radiation and in particular gamma radiation, especially that emitted by linear accelerators or by radionuclides that are in common use today. The irradiation of the tumor by radionuclides can be external or internal.

Preferably, the administration of the farnesyl transferase inhibitor commences up to one month, in particular up to 10 days or a week, before the tumor. Additionally, it is advantageous to fractionate the irradiation of the tumor and maintain the administration of the farnesyl transferase inhibitor in the interval between the first and the last irradiation session.

The amount of farnesyl protein transferase inhibitor, the dose of imdiation and the intermittence of the irradiation doses will depend on a series of parameters such as the type of tumor, its location, the patients' reaction to chemo- or radiotherapy and ultimately is for the physician and radiologists to determine in each individual case.

The present invention also concerns a method of cancer therapy for a host harboring a tumor comprising the steps of
administering a radiation-sensitizing effective amount of a farnesyl protein transferase inhibitor according to the invention before, during or after
administering radiation to said host in the proximity to the tumor.

In view of their useful pharmacological properties, the subject compounds may be formulated into various pharmaceutical fornn for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.01 mg/kg to 100 mg/kg body weight, and in particular from 0.05 mg/kg to 10 mg/kg body weight. It may be appropriate to administer the required dose as two, three, four or more sub-doses at appropriate intervals throughout the day. Said sub-doses may he formulated as unit dosage forms, for example, containing 0.5 to 500 mg, and in particular 1 mg to 200 mg of active ingredient per unit dosage form.

The following examples are provided for purposes of illustration.

Experimental Part

Hereinafter "THF" means tetrahydrofuran, "DIPE" meane diisopropylether, "DMF" means N,N-dimethylformamide, "EtOAc" means ethyl acetate, "BTEAC" means benzyltriethylammonium chloride and "BuLi" means n-butyl lithium.

A. PREPARATION OF THE INTERMEDIATES

EXAMPLE A1 a) NaOH (0.62 mol) was dissolved in methanol (100 m) and the mixture was cooled till room temperature. 1-Bromo-4-nitro-benzene (0.124 mol), followed by 3-chlorobenzeneacetonitrile (0.223 mol) were added dropwise, the temperature raised till 50° C. and the mixture was stirred at room temperature overnight. The mixture was poured into water and ice, the precipitate was filtered off, washed with water and extracted with $CH_2Cl_2$ and $CH_3OH$. The organic layer was dried ($MgSO_4$), filtered off and evaporated till dryness. The residue was taken up in diethyl ether, filtered off and dried, yielding 13.2 g (34.8%) of 5-bromo-3-(3-chlorophenyl)-2,1-benzisoxasole (intermediate 1), melting point: 163° C.

b) BuLi (0.0021 mol) was added dropwise at −70° C. to solution of intermediate 1 (0.0016 mol) in THF (5 ml). The mixture was stirred at −70° C. for 15 minutes. A solution of 2-thiophenecarboxaldehyde-5-chloro- (0.0019 mol) in THF (3 ml) was added dropwise. The mixture was stirred at −70° C. for 1 hour, poured out into ice water and extracted with $CH_2Cl_2$. The organic layer was separated, dried ($MgSO_4$), filtered, and the solvent was evaporated. This product was used without further purification, yielding 3-(3-chlorophenyl)-α-(5-chloro-2-thienyl)-2,1-benzisoxazole-5-methanol (intermediate 2).

c) $MnO_2$ (0.6 g) was added to a mixture of intermediate 2 (0.0016 mol) in dioxane (6 ml). The mixture was stirred and refluxed for 6 hours, then cooled and filtered over celite. The solvent was evaporated. The residue was crystallized from 2-propanone. The precipitate was filtered off and dried. The precipitate (0.6 g) was purified by column chromatography over silica gel (eluent: $CH_2Cl_2$/cyclohexane; 80/20 to 100; 15–35 μm). The fractions were collected and the solvent was evaporated. Yielding: 0.3 g (49%) of [3-(3-chlorophenyl)2,1-benzisoxazol-5-yl](5-chloro-2-thienyl)-methanone (intermediate 3), melting point: 176° C.

d) $TiCl_3$ 15% in water (130 ml) was added dropwise to a solution of intermediate 3 (0.0347 mol) in THF (130 ml). The mixture was stirred at room temperature overnight. $TiCl_3$ 15% in water (50 ml) was added. The mixture was stirred for a week-end, poured out into ice water, extracted with $CH_2Cl_2$, basified with $K_2CO_3$ 10%, extracted and washed with water. The organic layer was separated, dried ($MgSO_4$), filtered, and the solvent was evaporated, yielding 13 g (100%) of [4-amino-3-[1-(3-chlorobenzoyl)]phenyl](5-chloro-2-thienyl)-methanone (intermediate 4).

e) Trichloro-acetyl chloride, (0.0416 mol) then triethylamine (0.0416 mol) were added dropwise at 5° C. to a solution of intermediate 4 (0.0347 mol) in $CH_2Cl_2$ (130 ml) under $N_2$ flow. The mixture was stirred at room temperature overnight, poured out into water and extracted with $CH_2Cl_2$. The organic layer was separated, dried ($MgSO_4$), filtered, and the solvent was evaporated, yielding (100%) of 2,2,2-trichloro-N-[2-(3-chlorobenzoyl)-4-[(5-chloro-2-thienyl)carbonyl]phenyl]-acetamide (intermediate 5).

f) Ammonium acetate (0.0694 mol) was added to a solution of intermediate 5 (0.0347 mol) in dimethylsulfoxide (180 ml). The mixture was stirred at 60° C. for 4 hours, then cooled and poured out into ice water. The precipitate was filtered, taken up in $CH_3CN$ (warm), filtered, washed $CH_3CN$ and diethyl ether and dried under a vacuum, yielding 11.67 g (83.8%) of 4-(3-chlorophenyl)-6-[(5-chloro-2-thienyl)carbonyl]-2(1H)-quinazolinone (intermediate 6).

g) A mixture of intermediate 6 (0.0279 mol) in phosphoryl chloride (70 ml) was stirred at 100° C. for 2 hours and cooled. The solvent was evaporated. The residue was taken up in $CH_2Cl_2$. The solvent was evaporated. The residue was taken up in $CH_2Cl_2$, poured out into ice water, basified with $K_2CO_3$, extracted with $CH_2Cl_2$ and was washed with water. The organic layer was separated, dried ($MgSO_4$), filtered and the solvent was evaporated. The residue was crystallized from $CH_3CN$. The precipitate was filtered off and dried. Yielding: 10.35 g (88.4%) of [2-chloro-4-(3-chlorophenyl)-6-quinazolinyl](5-chloro-2-thienyl)-methanone (intermediate 7). The mother layer was evaporated. The residue was purified by colucolumn chromatography over silica gel (eluent: cyclohexane/EtOAc 90/10; 15–40 μm). The pure fractions were collected and the solvent was evaporated, yielding 0.4 g (3.4%) of [2-chloro-4-(3-chlorophenyl)-6-quinazolinyl](5-chloro-2-thienyl)-methanone (intermediate 7), melting point: 186 ° C.

h) BuLi (0.0404 mol) was added dropwise at −70° C. to a solution of 1-methyl-1H-imidazole (0.023 mol) in THF (40 ml) under $N_2$ flow. The mixture was stirred for 15 minutes. Chlorotriethyl-silane (0.0414 mol) was added dropwise. The mixture was stirred at −70° C. for 15 minutes. nBuLi (0.0356 mol) was added dropwise. The mixture was stirred for 15 minutes. A solution of intermediate 7 (0.023 mol) in THF (100 ml) was added at −70° C. The mixture was stirred at −70° C. for 1 hour, poured out in to water, extracted with $CH_2Cl_2$ and washed with water. The organic layer was separated, dried ($MgSO_4$), filtered, and the solvent was evaporated. The residue was purified by column chromatography over silica gel (eluent: $CH_2Cl_2/CH_3OH/NH_4OH$ 96/4/0.2; 15–40 μm). The fractions were collected and the solvent was evaporated. Yielding: 2.75 g (24%) of 2-chloro-4-(3-chlorpbenyl)-α-(5-chloro-2-thienyl)-α-(1-methyl-1H-imidazol-5-yl)-6-quinazolinemethanol (intermediate 8).

EXAMPLE A2 a) $TiCl_3$ 15% in water (1050 ml) was added at room temperature to a solution of (intermediate 1) (0.386 mol) in THF (1350 ml) and the mixture was stirred at room temperature for 2 h. The mixture was poured into water and ice and extracted with $CH_2Cl_2$. The organic layer was decanted, washed with $K_2CO_3$ 10%, dried ($MgSO_4$), filtered off and evaporated, yielding 102 g (85%) of (2-amino-5-bromophenyl) (3-chlorophenyl)-methanone (intermediate 9).

b) A solution of intermediate 9 (0.328 mol) and acetic acid anhydride (0.656 mol) in toluene (1200 ml) was stirred and refluxed for one night. The mixture was evaporated and the product was used without further purification, yielding 139 g (quant.) of N-[4-bromo-2-(3-chlorobenzoyl)phenyl]-acetamide (intermediate 10).

c) 2-methyl-2-propanol, potassium salt (1.635 mol) was added portionwise at room temperature to a solution of intermediate 10 (0.328 mol) in 1,2-dimethoxyethane (1200 ml) and the mixture was stirred at room temperature for one night. The mixture was evaporated till dryness, the residue was poured into water and ice and decanted. The oily residue was taken up in DIPE, the precipitate was filtered off, washed with EtOAc, $CH_3CN$ and diethyl ether and dried, yielding 88.6 g (80.76%) of 6-brome-4-(3-chlorophenyl)-2(1H)-quinolinone (intermediate 11).

d) A mixture of intermediated 11 (0.16 mol) in phosphoryl chloride (500 ml) was stirred and refluxed for one night. The mixture was evaporated till dryness, the residue was taken up in ice and water, alkalized with $NH_4OH$ and extracted with $CH_2Cl_2$. The organic layer was decanted, dried ($MgSO_4$), filtered off and evaporated, yielding 56 g (100%) of 6-bromo-2-chloro-4-(3-chlorophenyl)quinoline (intermediate 12).

e) $CH_3ONa$ 30%/$CH_3OH$ (96 ml) was added to a solution of intermediate 12 (0.16 mol) in methanol (500 ml) and the mixture was stirred and refluxed for one night. The mixture was evaporated till dryness, the residue was taken up in $CH_2Cl_2$, washed with water and decanted. The organic layer was dried ($MgSO_4$); filtered off and evaporated. The residue was taken up in diethyl ether and DIPE, the precipitate was filtered off and dried, yielding 48 g (86%) of 6-bromo-4-(3-chlorophenyl)-2-methoxyquinoline (intermediate 13).

f) Intermediate 13 (0.0287 mol) was dissolved in THF (100 ml) under $N_2$ flow. The mixture was cooled to −20° C. and then BuLi 1.6M in hexane was added dropwise. The mixture stood at −30° C. for 30 min., and then DMF (0.0574 mol) was added. The mixture was allowed to warm to room temperature, hydrolyzed and extracted with EtOAc. The organic layer was decanted, dried ($MgSO_4$), filtered, and the solvent was evaporated. The residue (10 g) was purified by column chromatography over silica gel (eluent: $CH_2Cl_2$/cyclohexane 60/40; 15–40 µm). The pure fractions were collected and the solvent was evaporated, yielding 7.5 g (88%) of 4-(3-chlorophenyl)-2-methoxy-6-quinolinecarboxaldehyde (intermediate 14).

g) A mixture of N-(1-methylethyl)-2-propanamine (0.0891 mol) in diethyl ether (270 mol) was cooled to −70° C. BuLi 1.6 M in hexane (0.0891 mol) was added dropwise. The mixture was stirred at −70° C. for 2 min. 2-Chlorothiophene (0.104 mol) was added. The mixture was stirred at −70° C. for 30 min. A solution of intermediate 14 (0.0742 mol) in THF (110 ml) was added dropwise. The mixture was stirred at −70° C. for 1 hour, brought to −30° C., hydrolyzed and extracted with EtOAc. The organic layer was separated, dried ($MgSO_4$), filtered and the solvent was evaporated till dryness. The residue (31.5 g) was purified by column chromatography over silica gel (eluent: cyclohexane/EtOAc 80/20; 20–45 µm). Two pure fractions were collected and their solvents were evaporated, yielding 21.7 g (70%) of 4-(3-chlorophenyl)-α-(5-chloro-2-thienyl)-2-methoxy-6-quinolinemethanol (intermediate 15).

h) A mixture of intermediate 15 (0.0521 mol) and $MnO_2$ (20 g) in trichloromethane (200 ml) was stirred and refluxed for several hours. The mixture was filtered over celite and the solvent was evaporated till dryness, yielding 21.7 g (100%) of [4-(3-chlorophenyl)-2-methoxy-6-quinolinyl] (5-chloro-2-thienyl)-methanone (intermediate 16).

i) A mixture of intermediate 16 (0.0521 mol) in HCl 3N (200 ml) and THF (200 ml) was stirred and refluxed for 48 hours and then poured out on ice. The precipitate was filtered off, washed with diethyl ether and dried, yielding 19.1 g (92%) of 4-(3-chlorophenyl)-6-[(5-2-thienyl)carbonyl]-2(1H)-quinolinone (intermediate 17), melting point: 260° C.

j) A mixture of intermediate 17 (0.0477 mol), iodomethane (0.0954 mol) and BTEAC (0.0239 mol) in THF (200 ml) and concentrated NaOH (200 ml) was stirred vigorously at room temperature for 1 hour. Water was added and the mixture was extracted with $CH_2Cl_2$ and $CH_3OH$. The organic layer was separated, dried ($MgSO_4$), filtered and the solvent was evaporated till dryness. The residue (32.3 g) was purified by column chromatography over silica gel (eluent $CH_2Cl_2$/EtOAc 85/15; 20–45 µm). The pure fractions were collected and the solvent was evaporated. The residue was taken up in diethyl ether. The precipitate was filtered off, washed with 2-propanone and diethyl ether and dried, yielding 18 g (91%) of 4-(3-chlorophenyl)-6-[(5-chloro-2-thienyl)carbonyl]-1-methyl-2(1H)-quinolinone (intermediate 18), melting point: 178° C.

k) BuLi (0.00472 mol) was added dropwise at −70° C. to a solution of 2,4-dihydro-4-methyl-3H-1,2,4-triazole-3-thione (0.00229 mol) in THF (6 ml) under $N_2$ flow. The mixture was stirred at −70° C. for 1 hour, then brought to 0° C., stirred at 0° C. for 1 hour and cooled to −70° C. Intermediate 18 (0.00121 mol) was added portionwise at −70° C. The mixture was stirred at −70° C. for 1 hour, brought slowly to 0° C., stirred at 0° C. for 1 hour and poured out into water. EtOAc was added. The mixture was extracted with EtOAc. The organic layer was washed with water, separated, dried ($MgSO_4$), filtered, and the solvent was evaporated. The residue was purified by column chromatography over silica gel (eluent: $CH_2Cl_2$/$CH_3OH$/$NH_4OH$ 90/10/1; 15–40 µm). The pure fractions were collected and the solvent was evaporated. The residue (0.17 g, 27%) was washed with diethyl ether, filtered and dried under a vacuum, yielding 0.13 g (20%) of 4-(3-chloropbenyl)-6-[(5-chloro-2-thienyl)hydroxy(5-mercapto-4-methyl-4H-1,2,4-triazol-3-yl)methyl]-1-methyl-2(1H)-quinolinone (intermediate 19).

EXAMPLE A3 a) BuLi 1.6M in hexane (0.0156 mol) was added dropwise at −70° C. to a mixture of 6-bromo-2-chloro-4(3-chlorophenyl)quinoline (0.0142 mol) in THF (70 ml) under $N_2$ flow. The mixture was stirred at −70° C. for 30 minutes. A solution of 3-furancarboxaldehyde (0.0212 mol) in THF (5 ml) was added dropwise. The mixture was stirred from −70° C. to room temperature for 2 hours. Water was added. The mixture was extracted with EtOAc. The organic layer was separated, dried ($MgSO_4$), filtered and the solvent was evaporated. The residue (5.8 g) was purified by column chromatography over silica gel (eluent: cyclobexane/EtOAc 70/30; 15–40 µm). The pure fractions were collected and the solvent was evaporated, yielding 3 g (57%) of 2-chloro-4-(3-chlorophenyl)-α-(3furanyl)-6-quinolinemethanol (intermediate 20), melting point: 162° C.

b) A mixture of intermediate 20 (0.0076 mol) and MnO$_2$ (0.03 mol) in dioxane (30 ml) was stirred and refluxed for 48 hours, cooled and filtered over celite. Celite was rinsed with CH$_2$Cl2. The solvent was evaporated. The residue was crystallized from 2-propanone/diethyl ether. The precipitate was filtered off and dried, yielding 0.93 g (33%) of [2-chloro-4-(3-chlorpbenyl)-6-quinolinyl]-3-furanyl-methanone (intermediate 21), melting point 152° C.

c) BuLi (0.0109 mol) was added dropwise at −70° C. to a solution of 1-methyl-1H -imidazole (0.0109 mol) in THF (13 ml) under N$_2$ flow. The mixture was stirred at −70° C. for 15 minutes. Chlorotriethyl-sllane (0.0112 mol) was added dropwise. The mixture was stirred at −70° C. for 15 minutes. BuL1 (0.0097 mol) was added dropwise. The mixture was stirred at −70° C. for 15 minutes. A solution of intermediate 21 (0.0062 mol) in THF (12 ml) was added at −70° C. The mixture was stirred at −70° C. for 30 minutes. Water was added. The mixture was extracted with EtOAc. The organic layer was separated, dried (MgSO$_4$), filtered, and the solvent was evaporated. The residue (4.2 g) was purified by column chromatography over silica gel (eluent: CH$_2$Cl$_2$/CH$_3$OH/NH$_4$OH 98/2/0.1; 15–40 μm). The fractions were collected and the solvent was evaporated. Yielding: 1.15 g 41%). A sample (0.6 g) was crystallized from 2-propanone. The precipitate was filtered off and dried, yielding 0.51 g of 2-chloro-4-(3-chlorophenyl)-α-(3-furanyl)-α-(1-methyl-1H-imidazol-5-yl)-6-quinolinemethanol (intermediate 22), melting point: 246° C.

EXAMPLE A4 a) BuLi (0.13 mol) was added dropwise at −78° C. to a solution of 5-bromo-3-(3-chlorophenyl)-2,1-benzisoxazole (0.113 mol) in THF (350 ml) under N$_2$ flow. The mixture was stirred at −70° C. for 15 minutes. A solution of 6-quinolinecarboxaldehyde (0.124 mol) in THF (200 ml) was added dropwise. The mixture was stirred at −78° C. for 1 hour, poured out into water and extracted with CH$_2$Cl$_2$. The organic layer was separated, dried (MgSO$_4$), filtered, and the solvent was evaporated. The residue was purified by column chromatography over silica gel (eluent: CH$_2$Cl$_2$/CH$_3$OH 100/0 to 98/2 to 0/100; 75–200 μm). Two fractions were collected and the solvent was evaporated, yielding 7 g of 5-bromo-3-(3-chlorophenyl)-2,1-benzisoxazole (starting material) and 31 g (70.9%) of α-[3-(3-chlorophenyl)-2,1-benzisoxazol-5-yl]-6-quinolinemethanol (intermediate 23).

b) MnO$_2$ (31 g) was added to a solution of intermediate 23 (0.08 mol) in dioxane (300 ml). The mixture was stirred and refluxed for 4 hours, cooled and filtered over celite. The solvent was evaporated. The residue was washed with 2-propanone, filtered off and dried, yielding 19.5 g (63.3%) of [3-(3-chlorophenyl)-2,1-benzisoxazol-5-yl]-6-quinolinyl-methanone (intermediate 24).

c) TiCl$_3$ 15% in water (20 ml) was added dropwise to a solution of intermediate 24 (0.0052 mol) in THF (20 ml). The mixture was stirred at room temperature overnight, poured out into ice water, extracted with CH$_2$Cl$_2$ and basified with K$_2$CO$_3$ 10%. The organic layer was separated, dried (MgSO$_4$), filtered, and the solvent was evaporated, yielding 2 g (100%) of [4-amino-3-[1-(3-chlorobenzoyl)]phenyl]-6-quinolinyl-methanone (intermediate 25).

d) Trichloro-acetyl chloride (0.0062 mol) then triethylamine (0.0062 mol) were added at 5° C. to a solution of intermediate 25 (0.00517 mol) in CH$_2$Cl$_2$ (20 ml) under N$_2$ flow. The mixture was brought to room temperature, stirred at room temperature for 3 hours, poured out into ice water and extracted with CH$_2$Cl$_2$. The organic layer was separated, dried (MgSO$_4$), filtered, and the solvent was evaporated, yielding 2.62 g (95%) of 2,2,2-trichloro-N-[2-(3-chlorobenzoyl)-4-(6-quinolinylcarbonyl)phenyl]-acetamide (intermediate 26).

e) A mixture of intermediate 26 (0.00492 mol) and ammonium acetate (0.00984 mol) in dimethylsulfoxide (25 ml) was stirred at 60° C. for 4 hours and poured out into ice water. The precipitate was filtered, taken up in acetonitrile (warm) and water, filtered and dried under a vacuum. A part (0.5 g) of this fraction (1 g, 49%) was purified by column chromatography over silica gel (eluent: CH$_2$Cl$_2$/CH$_3$OH/NH$_4$OH 95/5/0.1; 15–40 μm). The pure fractions were collected and the solvent was evaporated, yielding 0.2 g of 4-(3-chlorophenyl)-6-(6-quinolinylcarbonyl)-2 (1H)-quinazolinone (intermediate 27), melting point: >260° C.

f) A mixture of intermediate 27 (0.0325 mol) in phosphoryl chloride (80 ml) was stirred at 100° C. for 2 hours, then cooled and the solvent was evaporated. The residue was taken up in CH$_2$Cl$_2$, poured out into ice water, basified with K$_2$CO$_3$ 10% and extracted with CH$_2$Cl$_2$. The organic layer was washed with water, dried (MgSO$_4$), separated, dried (MgSO$_4$), filtered and the solvent was evaporated. The residue was purified by column chromatography over silica gel (eluent: cyclohexane/EtOAc 85/1; 15–35 μm). The pure fractions were collected and the solvent was evaporated, yielding 1 g of [2-chloro-4-(3-chlorophenyl)-6-quinazolinyl]-6-quinolinyl-methanone (intermediate 28), melting point: 170° C.

g) BuLi (0.0345 mol) was added dropwise at −70° C. to a solution of 1-methyl-1H-imidazole (0.0345 mol) in THF (30 ml) under N$_2$ flow. The mixture was stirred for 15 minutes. Chlorotriethyl-silane (0.0354 mol) was added dropwise. The mixture was stirred at −70° C. for 15 minutes. BuLi (0.0305 mol) was added dropwise. The mixture was stirred for 15 minutes. A solution of intermediate 28 (0.0197 mol) in THF (85 ml) was added dropwise at −70° C. The mixture was stirred at −70° C. for 1 hour, poured out into water, extracted with CH$_2$Cl$_2$ and washed with water. The organic layer was separated, dried (MgSO$_4$), filtered, and the solvent was evaporated. The residue was purified by column chromatography over silica gel (eluent: CH$_2$Cl$_2$/CH$_3$OH/NH$_4$OH 95/5/0.1; 15–35 μm). The fractions were collected and the solvent was evaporated. Yielding: 5.2 g (51%). A sample (2.9 g) was crystallized from 2-propanone. The precipitate was filtered off and dried, yielding 2.03 g of 2-chloro-4-(3-chlorophenyl)-α-(1-methyl-1H-imidazol-5-yl)-α-(6-quinolinyl)-6-quinazolinemethanol (intermediate 29), melting point 250° C.

EXAMPLE A5 a) BuLi (0.044 mol) was added dropwise at −70° C. to a solution of 5-bromo-3-(3-chlorophenyl)-2,1-benzisoxazole (0.044 mol) in THF (130 ml) under N$_2$ flow. The mixture was stirred at −70° C. for 15 minutes. A solution of (6-chloro-3-pyridinyl)(1-methyl-1H-imidazol-5-yl)-methanone (0.028 mol) in THF (80 ml) was added dropwise. The mixture was stirred at −70° C. for 1.5 hour, then poured out into water and extracted with CH$_2$Cl$_2$. The organic layer was separated, dried (MgSO$_4$), filtered, and the solvent was evaporated. The residue was purified by column chromatography over silica gel (eluent: CH$_2$Cl$_2$/CH$_3$OH/NH$_4$OH 97/3/0.1; 15–35 μm). The fractions were collected and the solvent was evaporated. Yielding: 2.5 g (21%). A sample (0.9 g) was crystallized from CH$_3$CN/diethyl ether. The precipitate was filtered off and dried, yielding 0.85 g of 3-(3-chlorophenyl)-α-(6-chloro-3-pyridinyl)-α-(1-methyl-1H-imidazol-5-yl)-2,1-benzisoxazole-5-methanol (intermediate 30), melting point 230° C.

b) TiCl$_3$ 15% in water (23 ml) was added dropwise at 5° C. to a mixture of intermediate 30 (0.0005 mol) in THF (23 ml). The mixture was stirred at 5° C. for 5 hours, poured out into ice water, basified with NaOH 3N and filtered over celite. The organic layer was washed with water, separated, dried (MgSO$_4$), filtered and the solvent was evaporated, yielding 1.5 g (66%) of [2-amino-5-[(6-chloro-3-pyridinyl)hydroxy(1-methyl-1H-imidazol-5-yl)methyl]phenyl](3-chlorophenyl)-methanone (intermediate 31).

c) Trichloro-acetyl chloride (0.003 mol) then triethylamine (0.003 mol) were added dropwise at 5° C. to a mixture of intermediate 31 (0.003 mol) in dichloromethane (15 ml) under N$_2$ flow. The mixture was stirred at room temperature for 5 hours, poured out into ice water and extracted with CH$_2$Cl$_2$. The organic layer was separated, dried (MgSO$_4$), filtered, and the solvent was evaporated, yielding 1.97 g (100%) of 2,2,2-trichloro-N-[2-(3-chlorobenzoyl)-4-[(6-chloro-3-pyridinyl)hydroxy(1-methyl-1H-imidazol-5-yl)methyl]phenyl]-acetamide (intermediate 32).

EXAMPLE A6 a) Trichloro-acetyl chloride (0.224 mol) was added dropwise at 5° C. to a mixture of (2-amino-5-bromophenyl)(3-chlorophenyl)-methanone (0.187 mol) in dichloromethane (520 ml). The mixture was stirred for 20 minutes. Triethylamine (0.224 mol) was added dropwise. The mixture was stirred at room temperature for 1 hour and 30 minutes, poured out into ice water and extracted with EtOAc. The organic layer was separated, washed with water, dried (MgSO$_4$), filtered and the solvent was evaporated, yielding 81 g (95%) of N-[4-bromo-2-(3-chlorobenzoyl)phenyl]-2,2,2-trichloro-acetamide (intermediate 33). The product was used without further purification in the next reaction step.

b) A mixture of intermediate 33 (0.160 mol) and acetic acid, ammonium salt (0.320 mol) in dimethylsulfoxide (500 ml) was stirred at 120° C. for 1 hour then cooled and poured out into ice water. The precipitate was filtered, washed with water (4 liters) then with acetonitrile and dried, yielding 42 g (79%). A part (1 g) of the residue (84 g, 79%) was crystallized from CH$_3$CN/CH$_3$OH. The precipitate was filtered off and dried, yielding 0.43 g of 6-bromo-4-(3-chlorophenyl)-2(1H)-quinazolinone (intermediate 34), melting point 281° C.

c) A mixture of intermediate 34 (0.06 mol) in phosphoryl chloride (100 ml) was stirred and refluxed for 1 hour and 30 minutes then cooled. The solvent was evaporated. The residue was taken up several times in CH$_2$Cl$_2$. The solvent was evaporated, yielding 24 g (quantitative) of 6-bromo-2-chloro-4-(3-chlorophenyl)-quinazoline (intermediate 35). The product was used without further purification in the next reaction step.

d) CH$_3$OH (200 ml) was added slowly at 5° C. to intermediate 35 (0.06 mol). The mixture was stirred at 5° C. for 15 minutes. CH$_3$ONa/CH$_3$OH (0.36 mol) was added dropwise slowly at 5° C. then brought to room temperature, stirred and refluxed for 1 hour, cooled, poured out into ice water and extracted with CH$_2$Cl$_2$. The organic layer was separated, dried (MgSO$_4$), filtered, and the solvent was evaporated. The residue (21 g) was crystallized from DIPE. The precipitate was filtered off and dried, yielding 17.7 g (84%) of 6-bromo-4-(3-chlorophenyl)-2-methoxy-quinoline (intermediate 36), melting point 132° C.

e) A mixture of intermediate 36 (0.0315 mol), Pd(PPh$_3$)$_4$ (0.00315 mol) and N-methoxy-methanamine (0.069 mol) in triethylamine (22 ml) and dioxane (100 ml) was stirred at 100° C. for 18 hours under a 5 bar pressure of CO, then cooled, poured out into ice water, extracted with CH$_2$Cl$_2$ and filtered over celite. The organic layer was separated, dried (MgSO$_4$), filtered and the solvent was evaporated. The residue was purified by column chromatography over silica gel (eluent: CH$_2$Cl$_2$/EtOAc 85/15 then CH$_2$Cl$_2$/CH$_3$OH/NH$_4$OH 98/2/0.4; 15–35 μm). The fractions were collected and the solvent was evaporated, yielding 3 g (27%) of 4-(3-chlorophenyl)-N,2-dimethoxy-N-methyl-6-quinazolinecarboxamide (intermediate 37), melting point: 118° C.

f) Phosphoryl chloride (0.084 mol) was added dropwise at room temperature to a solution of intermediate 37 (0.042 mol) in DMF (110 ml). The mixture was stirred at 80° C. for 4 hours, cooled, poured out into ice water, extracted with EtOAc and basified with K$_2$CO$_3$ solid. The organic layer was separated, dried (MgSO$_4$), filtered, and the solvent was evaporated. The residue was crystallised from DMF. The precipitate was filtered off and dried. Part (0.15 g) of the residue (9 g/59%) was dried at 90° C. under a vacuum, yielding 0.12 g of 2-chloro-4-(3-chlorophenyl)-N-methoxy-N-methyl-6-quinazolinecarboxamide (intermediate 38), melting point 110° C.

g) BuLi 1.6M in hexane (0.042 mol, 26.2 ml) was added dropwise at −70° C. to a mixture of 1-methyl-1H-imidazole (0.042 mol) in THF (80 ml) under N$_2$ flow. The mixture was stirred for 15 minutes. Chlorotriethyl-silane (0.043 mol) was added. The mixture was stirred for 15 minutes. BuLi 1.6M in hexane (0.037 mol, 23.2 ml) was added at −70° C. The mixture was stirred for 15 minutes. A solution of intermediate 38 (0.024 mol) in THF (80 ml) was added at −70° C. The mixture was stirred at −70° C. for 30 minutes, poured out into water and extracted with EtOAc. The organic layer was separated, dried (MgSO$_4$), filtered, and the solvent was evaporated. The residue (13 g) was purified by column chromatography over silica gel (eluent: CH$_2$Cl$_2$/CH$_3$OH 97/3; 15–35 μm). Two fractions were collected and the solvent was evaporated, yielding 1.4 g F1 and 2.4 g F2 Each fraction was purified by column chromatography over silica gel (eluent: CH$_2$Cl$_2$/EtOAc 50/50 then CH$_2$Cl$_2$/CH$_3$OH 97/3; 15–40 μm). The fractions were collected and the solvent was evaporated, yielding 2.46 g (27%) of [2-chloro-4-(3-chlorophenyl)-6-quinazolinyl](1-methyl-1H-imidazol-5-yl)-methanone (intermediate 39), melting point: 190° C.

h) A toluene solution (20%) of Hydrobis (2-methylpropyl)-aluminum (10 ml) was added dropwise at −70° C. to a mixture of intermediate 39 (0.012 mol) in THF (150 ml) under N$_2$ flow. The mixture was stirred at −70° C. for 30 minutes. Hydrobis(2-methylpropyl)-aluminum (50 ml) was added. The mixture was stirred at −70° C. for 3 hours, poured out into ice water, extracted with CH$_2$Cl$_2$ and filtered over celite. The organic layer was separated, dried (MgSO$_4$), filtered, and the solvent was evaporated, yielding 4 g (86%) of 2-chloro-4-(3-chlorophenyl)-α-(1-methyl-1H-imidazol-5-yl)-6-quinazolinemethanol (intermediate 40), melting point 140° C.

i) NaN$_3$ (0.031 mol) was added at room temperature to a mixture of intermediate 40 (0.0103 mol) in DMF (40 ml). The mixture was stirred at 90° C. for 4 hours, then cooled, poured out into ice water and stirred at room temperature for 1 hour. The precipitate was filtered off and dried at 80° C. under a vacuum, yielding 3.4 g (84%) of 5-(3-chlorophenyl)-α-(1-methyl-1H-imidazol-5-yl)-tetrazolo[1,5-a]quinazoline-7-methanol (intermediate 41), melting point 190° C.

j) A mixture of intermediate 41 (0.0025 mol) in thionyl chloride (10 ml) was stirred at 65° C. for 4 hours, then cooled and the solvent was evaporated till dryness. The residue was taken up twice in CH$_2$Cl$_2$. The solvent was evaporated till dryness, yielding 7-[chloro(1-methyl-1H-imidazol-5-yl)methyl]-5-(3-chlorophenyl)-tetrazolo[1,5-a]quinazoline as a hydrochloride salt (intermediate 42).

B. PREPARATION OF THE FINAL COMPOUNDS

EXAMPLE B1

A mixture of intermediate 8 (0.0040 mol) and sodium azide (0.0119 mol) in DMF (40 ml) was stirred at 90° C. for 3 hours, cooled and poured out into ice water. The precipitate was filtered. The filtrate was extracted with CH$_2$Cl$_2$. The organic layer was brought together with the precipitate dissolved in CH$_2$Cl$_2$. The organic layer was separated, dried (MgSO$_4$), filtered, and the solvent was evaporated. The residue was crystallized from CH$_3$CN/DIPE. The precipitate was filtered off and dried, yielding 1.33 g (66%) of 5-(3-chlorophenyl)-α-(5-chloro-2-thienyl)-α-(1-methyl-1H-imidazol-5-yl)-)tetrazolo[1,5-a]quinazoline-7-methanol (compound 1), melting point: 202° C.

EXAMPLE B2

Sodium nitrite (0.00025 mol) was added at 5° C. to a mixture of nitric acid (0.5 ml) in water (0.5 ml). A solution of intermediate 19 (0.00025 mol) in THF (1.5 ml) was added dropwise at 5° C. The mixture was stirred at 5° C. for 30 minutes, poured out into ice water, basified with K$_2$CO$_3$ 10% and extracted with EtOAc. The organic layer was washed with H$_2$O, separated, dried (MgSO$_4$), filtered, and the solvent was evaporated. The residue was purified by column chromatography over silica gel (eluent: CH$_2$Cl$_2$/CH$_3$OH 100/0 to 90/10; 10 μm). The pure fractions were collected and the solvent was evaporated, yielding 0.04 g (33%) of 4-(3-chlorophenyl)-6-[(5-chloro-2-thienyl)hydroxy(4-methyl-4H-1,2,4-triazol-3-yl)methyl]-1-methyl-2(1H)-quinolinone (compound 2) MS (MH$^+$):496, 498, 500.

EXAMPLE B3 a) A mixture of intermediate 22 (0.0022 mol) and NaN$_3$ (0.0066 mol) in DMF (10 ml) was stirred at 140° C. for 3 hours, cooled, poured out into water and stirred. The precipitate was filtered, washed with water, then with diethyl ether and dried. The residue (0.94 g, 93%) was crystallized from 2-propanone. The precipitate was filtered off and dried, yielding 0.75 g (74%) of 5-(3-chlorophenyl)-α-(3-furanyl)-α-(1-methyl-1H-imidazol-5-yl)-tetrazolo[1,5-a]quinoline-7-methanol (compound 3), melting point: 188° C.

b) Compound 3 (0.00131 mol) was added at 5° C. in thionyl chloride (6 ml). The mixture was stirred at room temperature for 2 hours. Thionyl chloride was evaporated. The residue was taken up in CH$_2$Cl$_2$. The solvent was evaporated till dryness, yielding (100%) of 7-[chloro-3-furanyl(1-methyl-1H-imidazol-5-yl)methyl]-5-(3-chlorophenyl)-tetrazolo[1,5-a]quinoline (compound 4). The product was used without further purification.

c) NH$_3$/iPrOH (6 ml) was added dropwise at 5° C. to a solution of compound 4 (0.00131 mol) in THF (6 ml). The mixture was stirred at room temperature for 3 hours, poured out into water and extracted with EtOAc. The organic layer was separated, dried (MgSO$_4$), filtered, and the solvent was evaporated. The residue (0.6 g) was purified by column chromatography over silica gel (eluent: CH$_2$Cl$_2$/CH$_3$OH/NH$_4$OH 97/3/0.5; 15–40 μm). The pure fractions were collected and the solvent was evaporated, yielding 0.2 g (33%) of 5-(3-chlorophenyl)-α-(3-furanyl)-α-(1-methyl-1H-imidazol-5-yl)-tetrazolo[1,5-a]quinoline-7-methanamine (compound 5) MS (MH$^+$):455, 457.

EXAMPLE B4 a) A mixture of intermediate 29 (0.005 mol) in HCl 6N (50 ml) was stirred and refluxed for 18 hours, then cooled. The solvent was evaporated. The residue was taken up in a minimum of water, basified with K$_2$CO$_3$. The precipitate was filtered, washed with water and dried under a vacuo, yielding 2.5 g (100%) of 4-(3-chlorophenyl)-6-[hydroxy(1-methyl-1H-imidazol-5-yl)-6-quinolinylmethyl]-2(1H)-quinazolinone (compound 6).

b) A solution of BTEAC (0.0005 mol) in NaOH (25 ml) then iodomethane (0.006 mol) were added dropwise to a mixture of compound 6 (0.005 mol) in THF (25 ml). The mixture was stirred at room temperature for 24 hours, then poured out into water and extracted with CH$_2$Cl$_2$. The organic layer was separated, dried (MgSO$_4$), filtered and the solvent was evaporated. The residue was purified by column chromatography over silica gel (eluent: CH$_2$Cl$_2$/CH$_3$OH/NH$_4$OH 93/7/0.5; 15–40 μm). The fractions were collected and the solvent was evaporated, yielding: 0.656 g (26%) of 4-(3-chlorophenyl)-6-[hydroxy(1-methyl-1H-imidazol-5-yl)-6-quinolinylmethyl]-1-methyl-2(1H)-quinazolinone (compound 7), melting point: 192° C.

EXAMPLE B5

A mixture of intermediate 8 (0.0007 mol) in HCl 3N (5 ml) was stirred and refluxed for 30 minutes. The solvent was evaporated. The residue was taken up in a minimum of water, basified with K$_2$CO$_3$, filtered, rinsed with water and dried. The residue was purified by column chromatography over silica gel (eluent: CH$_2$Cl$_2$/CH$_3$OH/NH$_4$OH 90/10/0.2 to 50/50/1; 15–40 μm). The pure fractions were collected and the solvent was evaporated, yielding 0.323 g (83.8%) of 4-(3-chlorophenyl)-6-[(5-chloro-2-thienyl)hydroxy(1-methyl-1H-imidazol-5-yl)methyl]-2(1H)-quinazolinone (compound 8) MS (MH$^+$):482, 484, 486.

EXAMPLE B6

Ammonium acetate (0.006 mol) was added to a mixture of intermediate 32 (0.003 mol) in dimethylsulfoxide (20 ml).

The mixture was stirred at 60° C. for 4 hours, then cooled, poured out into ice water and filtered. The precipitate was taken up in CH₂Cl₂/toluene, filtered off and dried under a vacuo, yielding 0.66 g (42%) of 4-(3-chlorophenyl)-6-[(6-chloro-3-pyridinyl)hydroxy(1-methyl-1H-imidazol-5-yl) methyl]-2(1H)-quinazolinone (compound 9) MS (MH⁺): 477, 479, 481.

EXAMPLE B7

2-Phenyl-1H-imidazole (0.0038 mol) was added at room temperature to a mixture of intermediate 42 (0.0025 mol) in acetonitrile (10 ml). The mixture was stirred and refluxed for 2 hours, poured out into ice water and extracted with CH₂Cl₂/CH₃OH. The organic layer was washed with K₂CO₃, separated, dried (MgSO₄), filtered and the solvent was evaporated. The residue was purified by column chromatography over silica gel (eluent: CH₂Cl₂/CH₃OH/ NH₄OH 96/4/0.2; 15–40 μm). The pure fractions were collected and the solvent was evaporated. The residue (0.2 g) was dried at 80° C. for 3 hours, yielding 0.17 g (13%) of, 5-(3-chlorophenyl)-7-[(1-methyl-1H-imidazol-5-yl)(2-phenyl-1H-imidazol-1-yl)methyl]-tetrazolo[1,5-a]quinazoline (compound 10), melting point: 150° C.

Table F-1 lists the compounds that were prepared according to one of the above Examples. The following abbreviations were used in the tables:

TABLE F-1

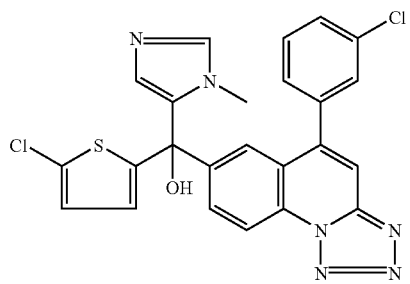

Co. No. 11; Ex. B1; mp. 232° C.

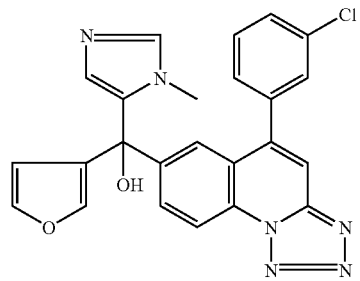

Co. No. 12; Ex. B1; mp. 188° C.

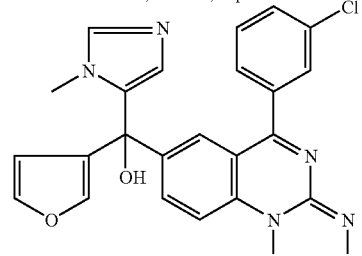

Co. No. 13; Ex. B1; mp. 228° C.

TABLE F-1-continued

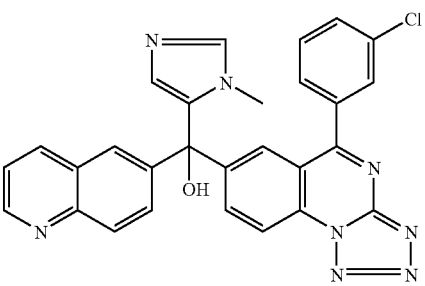

Co. No. 14; Ex. B1; mp. 200° C.

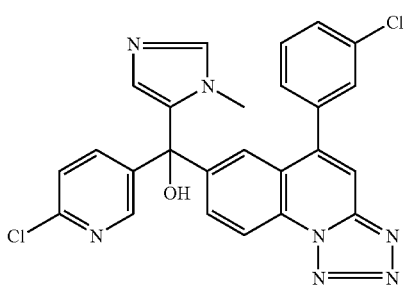

Co. No. 15; Ex. B1; mp. 245° C.

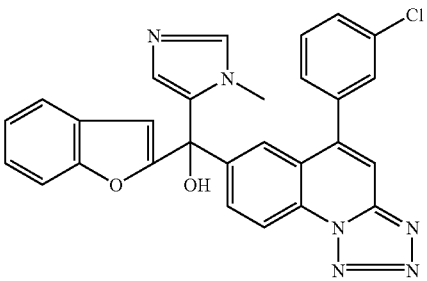

Co. No. 16; Ex. B1; mp. 192° C.

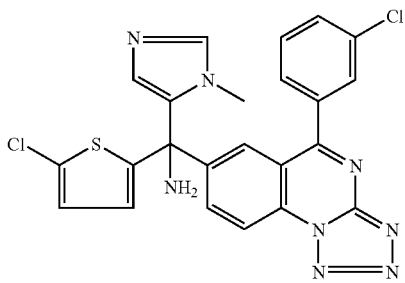

Co. No. 17; Ex. B3; mp. 220° C.

TABLE F-1-continued
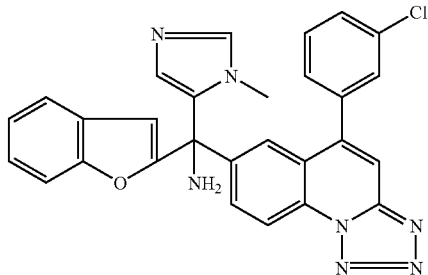
Co. No. 18; Ex. B3; MS (MH+): 505, 507
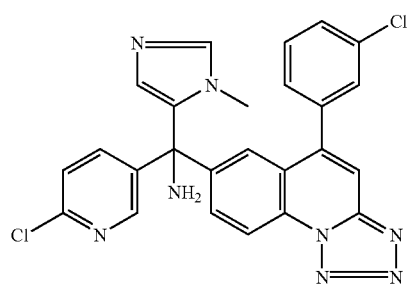
Co. No. 19; Ex. B3; MS (MH+): 500, 502 504
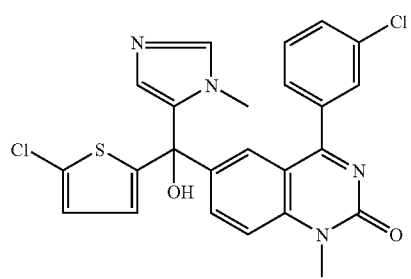
Co. No. 20; Ex. B4; mp. 160° C.
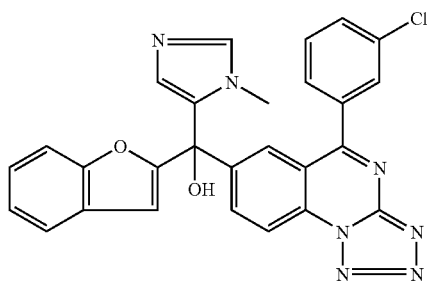
Co. No. 21; Ex. B1; mp. 210
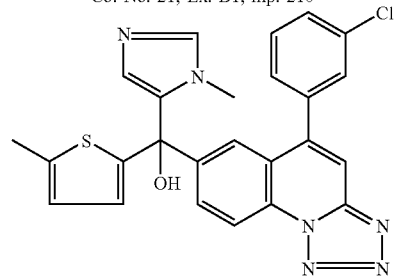
Co. No. 22; Ex. B1; mp. 218° C.
TABLE F-1-continued
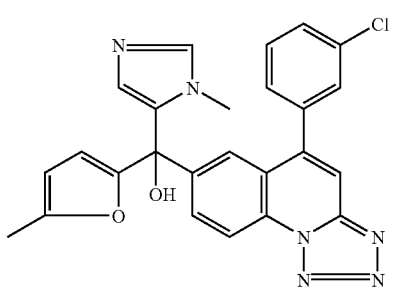
Co. No. 23; Ex. B1; mp. 242° C.
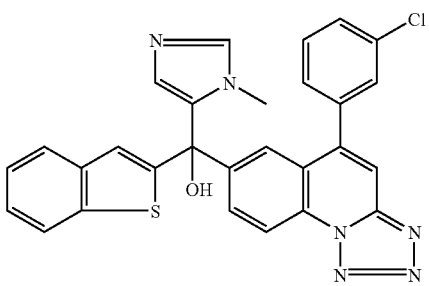
Co. No. 24; Ex. B1; mp. 192° C.
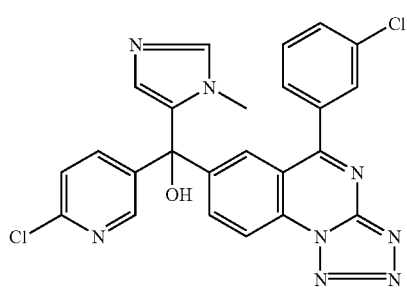
Co. No. 25; Ex. B1; mp. 190° C.
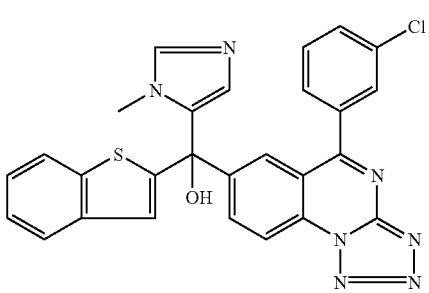
Co. No. 26; Ex. B1; mp. 200° C.
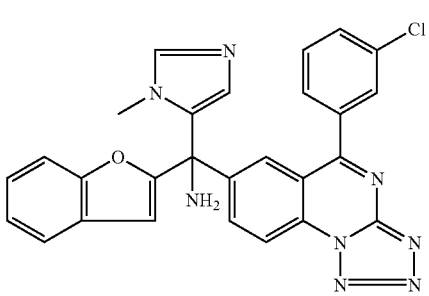

TABLE F-1-continued
Co. No. 27; Ex. B3; MS (MH+): 506, 508
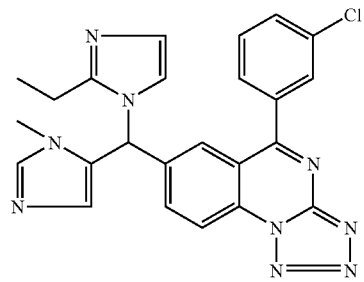
Co. No. 28; Ex. B7; mp. 120° C.
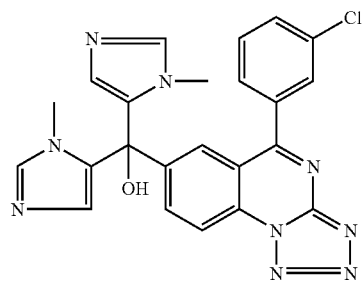
Co. No. 29; Ex. B1; mp. 220° C.
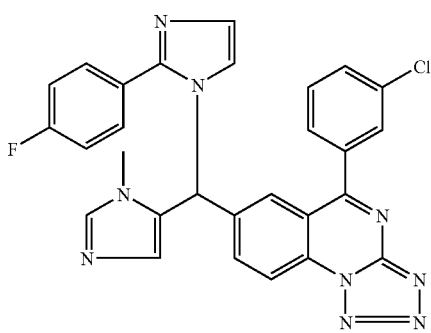
Co. No. 30; Ex. B7; mp. 154° C.
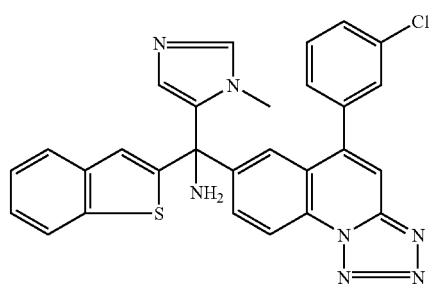
Co. No. 31; Ex. B3; mp. 254° C.
TABLE F-1-continued
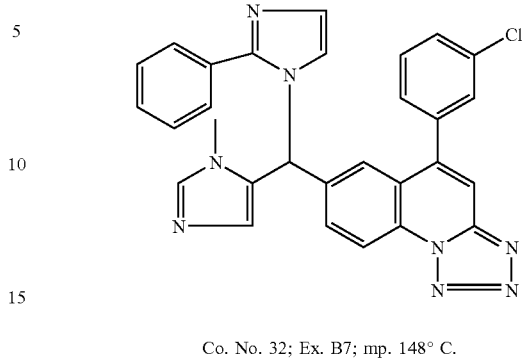
Co. No. 32; Ex. B7; mp. 148° C.
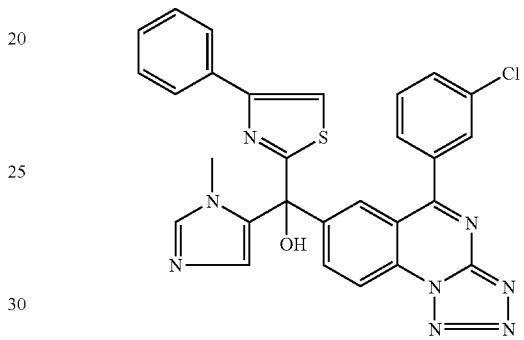
Co. No. 33; Ex. B1; mp. 178° C.
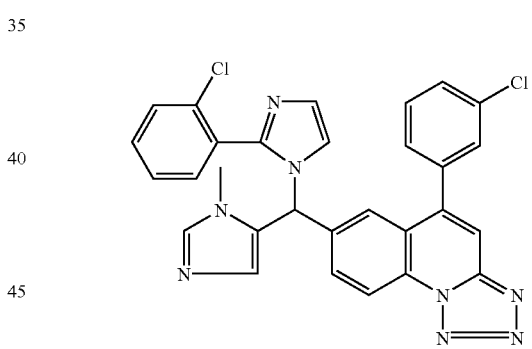
Co. No. 34; Ex. B7; mp. 177° C.
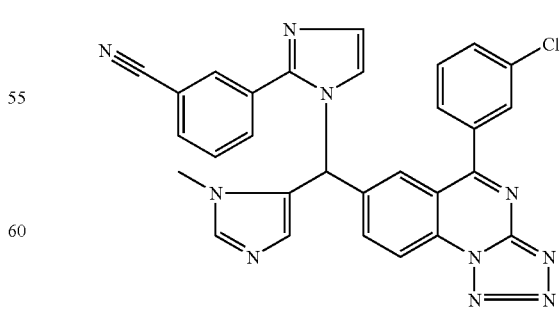
Co. No. 35; Ex. B7; MS (MH+): 542, 544

TABLE F-1-continued

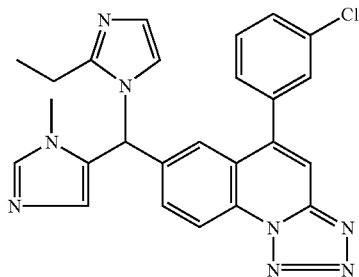

Co. No. 36; Ex. B7; MS (MH+): 468, 470

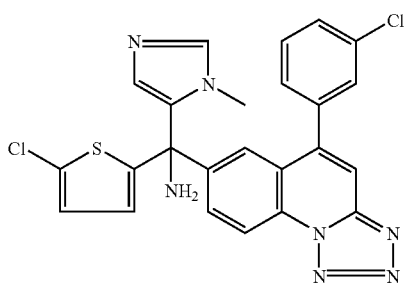

Co. No. 37; Ex. B3; mp. 208° C.

C. PHARMACOLOGICAL EXAMPLE

EXAMPLE C.1

In Vitro Assay for Inhibition of Farnesyl Protein Transferase

An in vitro assay for inhibition of farnesyl transferase was performed essentially as described in WO 98/40383, pages 33–34.

EXAMPLE C.2

Ras-transformed Cell Phenotype Reversion Assay

The ras-transformed cell phenotype reversion assay was performed essentially as described in WO 98/40383, pages 34–36.

EXAMPLE C.3

Farnesyl Protein Transferase Inhibitor Secondary Tumor Model

The farnesyl protein transferase inhibitor secondary tumor model was used as described in WO 98/40383, page 37.

D. COMPOSITION EXAMPLE

Film-coated Tablets

Preparation of Tablet Core

A mixture of 100 g of a compound of formula (I), 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

What is claimed is:

1. A compound of formula (I):

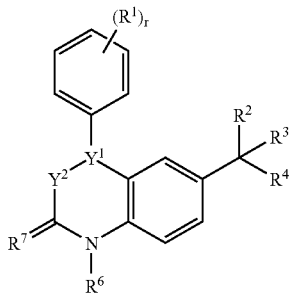

(I)

or a pharmaceutically acceptable salt or N-oxide or stereochemically isomeric form thereof, wherein r is 0 or 1;

$>Y^1-Y^2-$ is a trivalent radical of formula $>C=N-$(y-1);

$R^1$ is halo;

$R^2$ is a thiophene, furyl, pyridyl, diazolyl, oxazolyl, benzodiazolyl, benzotriazolyl, or quinolinyl group, optionally substituted by halo, cyano, $C_{1-6}$alkyl, or aryl;

$R^3$ is hydrogen, or a radical of formula

—O—$R^{10}$ (b-1) or

—$NR^{11}R^{12}$ (b-3);

wherein $R^{10}$ $R^{11}$ and $R^{12}$ are hydrogen;

and $R^{12}$ is hydrogen or hydroxyl;

$R^4$ is a radical of formula

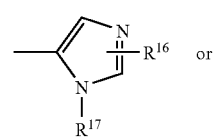

(c-2)

or

-continued

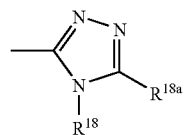
(c-3)

wherein
R$^{16}$ is hydrogen;
R$^{17}$ is C$_{1-6}$alkyl;
R$^{18}$ is C$_{1-6}$alkyl;
R$^{18a}$ is hydrogen;
R$^5$ is C$_{1-6}$alkyl, —CH$_2$—C$_{3-10}$cycloalkyl-, —C$_{1-6}$alkyl-Ar$^2$;
R$^7$ is oxygen;
or R$^6$ and R$^7$ together form a trivalent radical of formula:

—CR$^{30}$=N—N=  (x-2) or

—N=N—N=  (x-4)

wherein R$^{30}$ is hydrogen;
Ar is phenyl, or phenyl substituted by one to five substituents each independently selected from halo, hydroxy, cyano, nitro, C$_{1-6}$alkyl, haloC$_{1-6}$alkyl, -alkylNH$^2$, C$_{1-6}$alkyloxy, OCF$_3$, hydroxycarbonyl, C$_{1-6}$alkyloxycarbonyl, or a bivalent substituent of formula —O—CH$_2$—O— or —O—CH$_2$—CH$_2$—O—.

2. The compound of claim 1 in which
r is 1;
R$^2$ is a 4-chloro-thiophen-2-yl, 3-furyl, 5-chloro-pyrid-3-yl, 2-phenyl-imidazol-1-yl, 2-ethyl-imidazol-1-yl, benzimidazol-1-yl or 2-hydroxy-quinoline-7-yl group; or R$^6$ and R$^7$ together form a trivalent radical of forrnula —N=N—N=.

3. A compound selected from:
5-(3-chlorophenyl)-α-(5-chloro-2-thienyl)-α-(1-methyl-1H-imidazol-5-yl) -tetrazolo[1,5-a]quinazoline-7-methanol,
5-(3-chlorophenyl)-α-(3-furanyl)-α-(1-methyl-1H-imidazol-5-yl)-tetrazolo-[1,5-a]quinazoline-7-methanol,
5-(3-chlorophenyl)-α-(1-methyl-1H-imidazol-5-yl)-α-(6-quinolinyl)-tetrazolo-[1,5a]quinazoline-7-methanol,
5-(3-chlorophenyl)-α-(5-chloro-2-thienyl)-α-(1-methyl-1H-imidazol-5-yl) -tetrazolo[1,5-a]quinazoline-7-methanamine,
4-(3-chlorophenyl)-6-[(5-chloro-2-thienyl)hydroxy(1-methyl-1H-imidazol -5-yl)methyl]1-methyl-2(1H)-quinazolinone,
5-(3-chlorophenyl)-7-[(1-methyl-1H-imidazol-5-yl)(2-phenyl-1H-imidazol -1-yl)methyl]-tetrazolo[1,5-a]quinazoline,
α-(2-benzofuranyl)-5-(3-chlorophenyl)-α-(1-methyl-1H-imidazol-5-yl) -tetrazolo[1,5-a]quinazoline-7-methanamine,
5-(3-chlorophenyl)-7-[(2-ethyl-1H-imidazol-1-yl)(1-methyl-1H-imidazol -5-yl)methyl]-tetrazolo[1,5-a]quinazoline,
5-(3-chlorophenyl)-α, α-bis(1-methyl-1H-imidazol-5-yl)-tetrazolo[-1,5-a]quinazoline-7-methanol,
5-(3-chlorophenyl)-7-[[2-(4-fluorophenyl)-1H-imidazol-1-yl](1-methyl -1H-imidazol-5-yl)methyl]-tetrazolo[1,5-a]quinazoline,
3-[1-[[5-(3-chlorophenyl)tetrazolo[1,5-a]quinazolin-7-yl](1-methyl-1H-imidazol-5-yl)methyl]-1H-imidazol-2-yl]-benzonitrile,
and their pharmaceutically acceptable salts.

4. A pharmaceutical composition comprising a pharmaceutically acceptable carrier, and an active ingredient comprising a therapeutically effective amount of a compound of claim 1.

5. A pharmaceutical composition comprising a pharmaceutically acceptable carrier, and an active ingredient comprising a therapeutically effective amount of a compound of claim 2.

6. A pharmaceutical composition comprising a pharmaceutically acceptable carrier, and an active ingredient comprising a therapeutically effective amount of a compound of claim 3.

7. A method for treating colon and pancreatic carcinomas comprising administering an effective amount of a compound according to claim 1 to a subject in need of such treatment.

8. A method for treating colon and pancreatic carcinomas comprising administering an effective amount of a compound according to claim 2 to a subject in need of such treatment.

9. A method for treating colon and pancreatic carcinomas comprising administering an effective amount of a compound according to claim 3 to a subject in need of such treatment.

* * * * *